United States Patent
Meng et al.

(10) Patent No.: US 10,866,229 B2
(45) Date of Patent: Dec. 15, 2020

(54) SYSTEMS AND METHODS FOR GENOME MAPPING

(71) Applicant: Massachusetts Institute of Technology, Cambridge, MA (US)

(72) Inventors: Huaiyu Meng, Medford, MA (US); Rajeev Ram, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 375 days.

(21) Appl. No.: 15/883,183

(22) Filed: Jan. 30, 2018

(65) Prior Publication Data
US 2018/0217122 A1    Aug. 2, 2018

Related U.S. Application Data

(60) Provisional application No. 62/452,181, filed on Jan. 30, 2017.

(51) Int. Cl.
*G01N 33/487*      (2006.01)
*G01N 27/447*      (2006.01)
(Continued)

(52) U.S. Cl.
CPC .... *G01N 33/48707* (2013.01); *B01L 3/50273* (2013.01); *B01L 3/502715* (2013.01);
(Continued)

(58) Field of Classification Search
CPC ....... G01N 33/48707; G01N 27/44791; G01N 27/44713; G01N 27/44726;
(Continued)

(56) References Cited

U.S. PATENT DOCUMENTS

2004/0197843 A1*   10/2004   Chou .................. G01N 21/648
                                                    435/7.92
2005/0156192 A1    7/2005   Ko et al.
(Continued)

FOREIGN PATENT DOCUMENTS

WO    WO 2016/049544 A1    3/2016

OTHER PUBLICATIONS

Cheng et al., "Rapid identification of bacterial utilizing amplified dielectrophoretic force-assisted nanoparticle-induced surface-enhanced Raman spectroscopy," Nanoscale Research Letters 9:324, http://www.nanoscaleresletter.com/content/9/1/324, 8 pages (2014).
(Continued)

*Primary Examiner* — Lore R Jarrett
(74) *Attorney, Agent, or Firm* — Smith Baluch LLP

(57) ABSTRACT

A system for molecular mapping includes a semiconductor substrate defining a reservoir to receive a sample of molecules and a nanofluidic channel in fluid communication with the reservoir. The system also includes a plurality of electrodes, in electrical communication with the nanofluidic channel, to electrophoretically trap the sample of molecules in the nanofluidic channel. At least one avalanche photodiode is fabricated in the semiconductor substrate and disposed within an optical near-field of the nanofluidic channel to detect fluorescence emission from at least one molecule in the sample of molecules.

21 Claims, 24 Drawing Sheets

(51) Int. Cl.

| | | |
|---|---|---|
| *B03C 5/02* | (2006.01) | |
| *B01L 3/00* | (2006.01) | |
| *B81C 1/00* | (2006.01) | |
| *B03C 5/00* | (2006.01) | |
| *C12Q 1/6876* | (2018.01) | |
| *H01L 31/02* | (2006.01) | |
| *H01L 31/107* | (2006.01) | |
| *H01L 31/16* | (2006.01) | |
| *B82B 1/00* | (2006.01) | |
| *B82B 3/00* | (2006.01) | |
| *B82Y 15/00* | (2011.01) | |
| *B82Y 40/00* | (2011.01) | |

(52) U.S. Cl.
CPC ........ *B01L 3/502761* (2013.01); *B03C 5/005* (2013.01); *B03C 5/026* (2013.01); *B81C 1/00246* (2013.01); *C12Q 1/6876* (2013.01); *G01N 27/44713* (2013.01); *G01N 27/44726* (2013.01); *H01L 31/02005* (2013.01); *H01L 31/02019* (2013.01); *H01L 31/107* (2013.01); *H01L 31/165* (2013.01); *B01L 2200/0663* (2013.01); *B01L 2300/0816* (2013.01); *B01L 2300/0896* (2013.01); *B01L 2400/0421* (2013.01); *B01L 2400/0424* (2013.01); *B03C 2201/26* (2013.01); *B81B 2201/058* (2013.01); *B81B 2203/0338* (2013.01); *B81C 2203/0742* (2013.01); *B82B 1/001* (2013.01); *B82B 3/0019* (2013.01); *B82Y 15/00* (2013.01); *B82Y 40/00* (2013.01); *G01N 27/44791* (2013.01)

(58) Field of Classification Search
CPC .. G01N 21/6402; G01N 21/645; G01N 21/05; G01N 2021/0346; B81C 2203/0742; B81C 1/00246; H01L 31/165; H01L 31/107; H01L 31/02019; H01L 31/02005; H01L 31/101; C12Q 1/6876; B01L 2300/0896; B01L 2200/0663; B01L 2400/0421; B01L 2400/0424; B01L 2300/0816; B01L 3/502715; B01L 3/50273; B01L 3/502761; B01L 2200/027; B01L 2200/10; B01L 2400/043; B01L 3/502792; B01L 2200/0647; B01L 2300/0654; B03C 2201/26; B03C 5/026; B03C 5/005; B82Y 40/00; B82Y 15/00; B82B 3/0019; B82B 1/001; B81B 2201/058; B81B 2203/0338; H02M 3/156

See application file for complete search history.

(56) References Cited

U.S. PATENT DOCUMENTS

| | | | |
|---|---|---|---|
| 2009/0050934 A1* | 2/2009 | Sadygov ........... | H01L 31/03529 257/186 |
| 2010/0019128 A1 | 1/2010 | Itzler | |
| 2010/0029508 A1* | 2/2010 | Austin .................. | B82Y 30/00 506/16 |
| 2010/0200781 A1 | 8/2010 | Khorasani et al. | |
| 2013/0176563 A1* | 7/2013 | Ozawa ................ | C12Q 1/6869 356/301 |
| 2014/0252524 A1* | 9/2014 | Sanfilippo ............. | H01L 31/107 257/432 |
| 2014/0272958 A1 | 9/2014 | Ramsey et al. | |
| 2014/0306314 A1* | 10/2014 | Yamamoto ........ | H01L 27/14609 257/448 |
| 2019/0025214 A1* | 1/2019 | Rothberg ............ | H01S 5/02461 |

OTHER PUBLICATIONS

Devadjasan et al., "Overview of CMOS image sensor use in molecular diagnostics," Curr Appl Phys 15, 402-411 (2015).

Field et al., "A 100 fps, Time-Correlated Single-Photon-Counting-Based Fluorescence-Lifetime Imager in 130 nm CMOS," IEEE J Solid-St Circ 49, 867-880 (2014).

Field et al., "A low-noise, single-photon avalanche diode in standard 0.13 µM complementary metal-oxide-semiconductor process," Appl Phys Lett 97, 211111, https://doi.org/10.1063/1.3518473, 4 pages. (2010).

Georgas et al., "A Monolithically-Integrated Optical Receiver in Standard 45-nm SOI," IEEE J Solid-St Circ 47, 1693-1702 (2012).

Gunn et al., "CMOS Photonics or High-Speed Interconnects," Micro 26, 58-66 (2006).

Holzel et al., "Trapping single molecules by dielectrophoresis," Phys Rev Lett 95, 128102-1-4 (2005).

Hughes et al., "Dielectrophoretic trapping of single sub-micrometre scale bioparticles," J Phys D Appl Phys 31, 2205-2210 (1998).

International Search Report and Written Opinion dated May 16, 2018 for International Application No. PCT/US2018/015878, 12 pages.

Jeffet et al., "Super-Resolution Genome Mapping in Silicon Nanochannels," ACS Nano, 10, 9823-9830 (2016).

Kimerling et al., "Electronic-photonic integrated circuits on the CMOS platform," in Integrated Optoelectronic Devices 2006, (International Society for Optics and Photonics, 1996), 612502-612502.

Lam et al., "Genome mapping on nanochannel arrays for structural variation analysis and sequence assembly," Nature Biotechnol. 30, 771-776 (2012).

Meenehan et al., "Trapped Atoms in One-Dimensional Photonic Crystals," in CLEO:QELS, Fundamental Science, Optical Society of America, QTh4C.6, 2 pages (2013).

Mehta et al., "Fano line shapes in transmission spectra of silicon photonic crystal resonators," Appl Phys Lett 102, https://doi.org/10.1063/1.4794064, 5 pages (2013).

Mehta et al., "Integrated optical addressing of an ion qubit," Nat Nanotechnol 11, 1066-1071 (2016).

Merriman et al., "Progress in Ion Torrent semiconductor chip based sequencing," Electrophoresis 33, 3397-3417 (2012).

Orcutt et al., "Open foundry platform for high-performance electronic-photonic integration," Optics Express 20, 12222-12232 (2012).

Orcutt et al., "Photonic device layout within the foundry CMOS design environment," IEEE Photonics Technology Letters 22, 544-546 (2010).

Pavanello et al., "Depletion-Based Optical Modulators in a Bulk 65 nm CMOS Platform," in Optical Fiber Communication Conference, OSA Technical Digest, Optical Society of America, Th4H.3, 3 pages (2016).

Perez-Pinera et al., "Synthetic biology and microbioreactor platforms for programmable production of biologics at the point-of-care," Nature Communications 7, https://doi:10.1038/ncomms12211, 10 pages (2016).

Quail et al., "A tale of three next generation sequencing platforms: comparison of Ion Torrent, Pacific Biosciences and Illumina MiSeq sequencers," BMC Genomics 13, 341, 13 pages (2012).

Rhoads et al., "PacBio Sequencing and Its Applications," Genomics, Proteomics & Bioinformatics 13, 278-289 (2015).

Rothberg et al., "An integrated semiconductor device enabling non-optical genome sequencing," Nature 475, 348-352 (2011).

Seo et al., "De novo assembly and phasing of a Korean human genome," Nature 538, 243-247 (2016).

Shainline et al., "Depletion-mode carrier-plasma optical modulator in zero-change advanced CMOS," Opt Lett 38, 2657-2659 (2013).

Sun et al., "Single-chip microprocessor that communicates directly using light," Nature 528, 534-538 (2015).

Thompson et al., "Coupling a Single Trapped Atom to a Nanoscale Optical Cavity," Science 340, 1202-1205 (2013).

Vetsch et al., "Optical interface created by laser-cooled atoms trapped in the evanescent field surrounding an optical nanofiber," Physical Review Letters 104, 203603-1-4 (2010).

(56) References Cited

OTHER PUBLICATIONS

Vlasov et al., "High-throughput silicon nanophotonic wavelength-insensitive switch for on-chip optical networks," Nature Photonics 2, 242-246 (2008).

Zortman et al., "Monolithic Integration of Silicon Electronics and Photonics," in Winter Topicals, Digest of Technical Papers, IEEE, 139-140 (2011).

\* cited by examiner

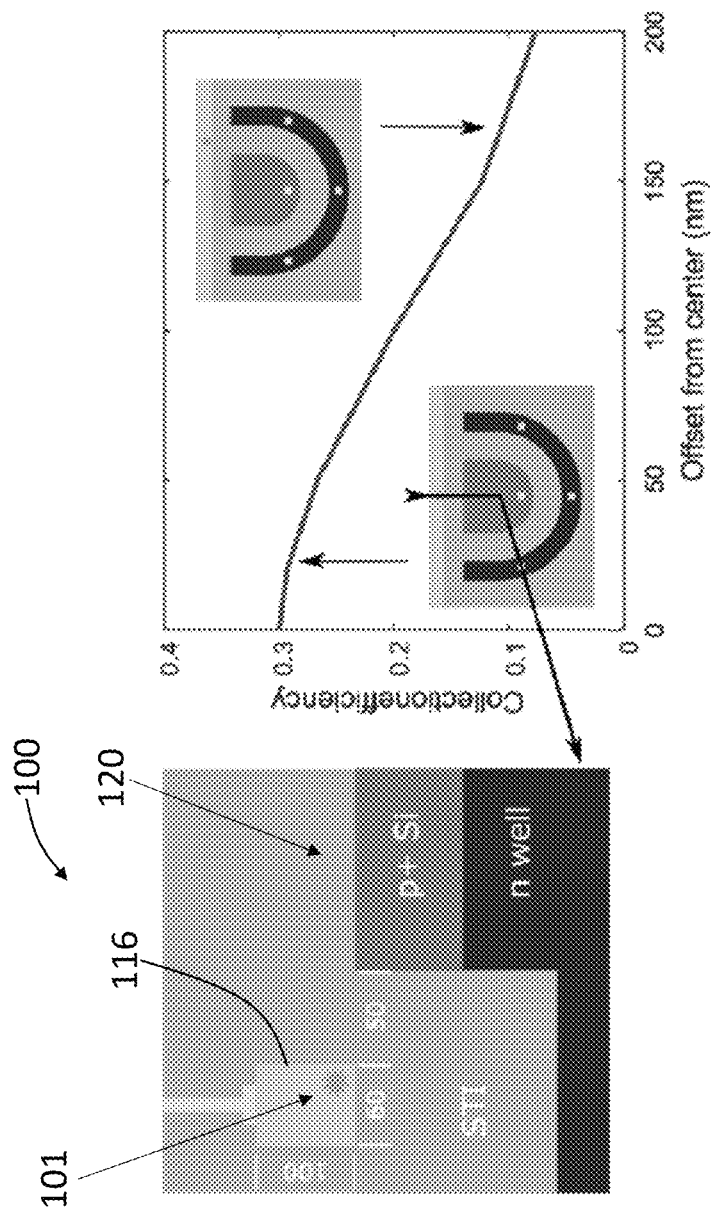
*FIG. 2A*  *FIG. 2B*  *FIG. 2C*

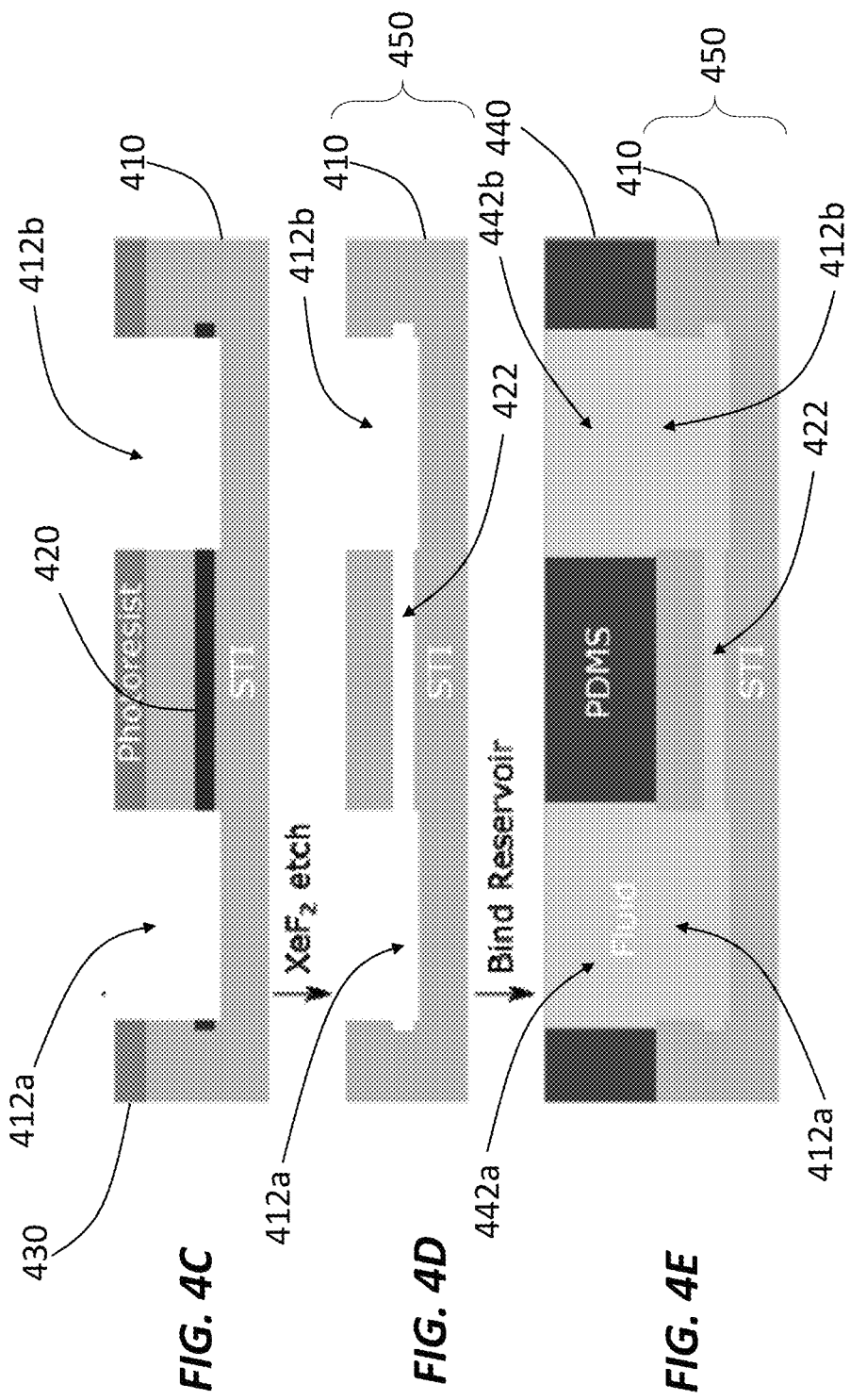

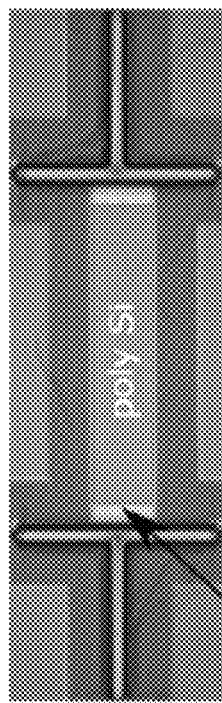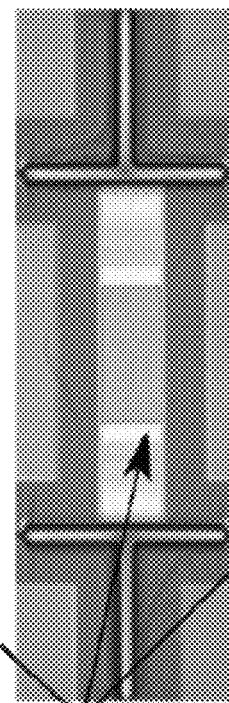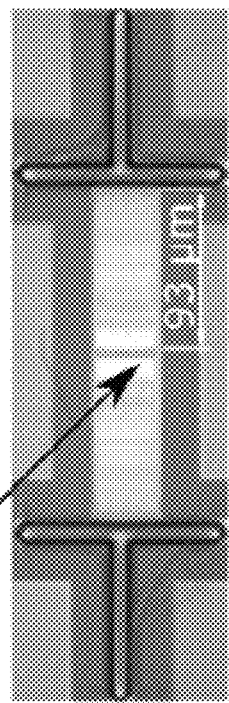
FIG. 5A — 20s x 10 cycles
FIG. 5B — 20s x 50 cycles
FIG. 5C — 20s x 110 cycles
Etch Front

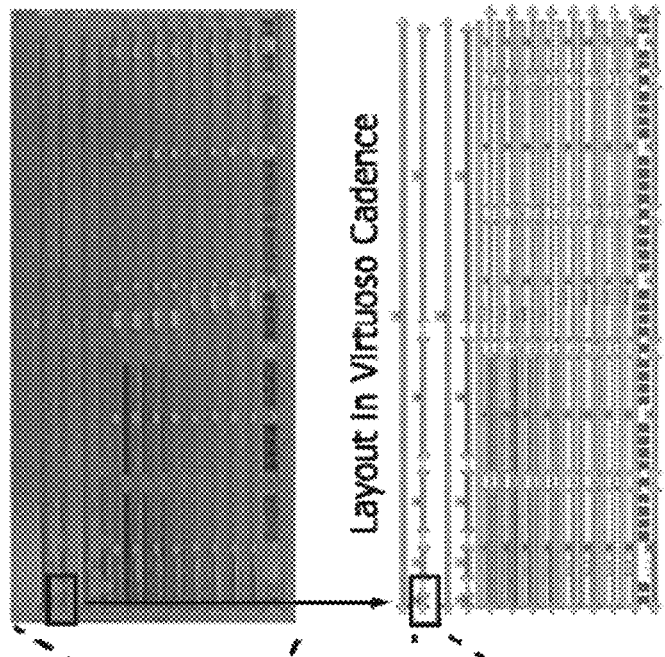
*FIG. 6C*  *FIG. 6D*
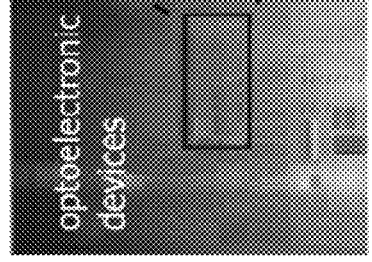
*FIG. 6B*
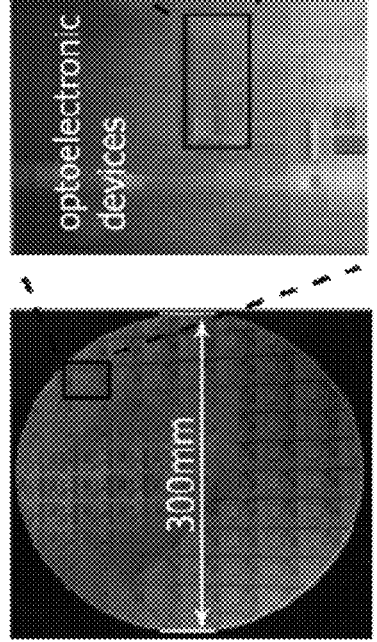
*FIG. 6A*
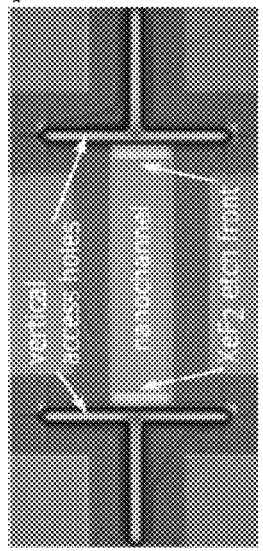
*FIG. 6E*

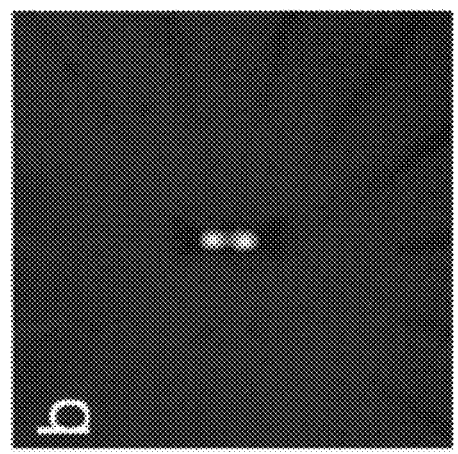
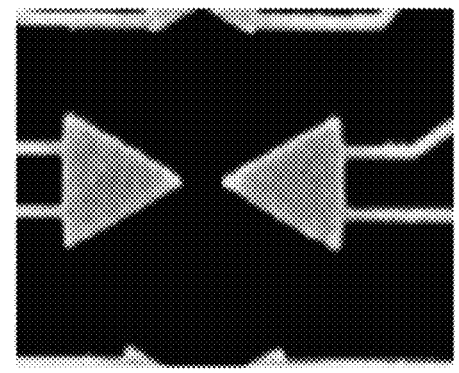
FIG. 10A
FIG. 10B

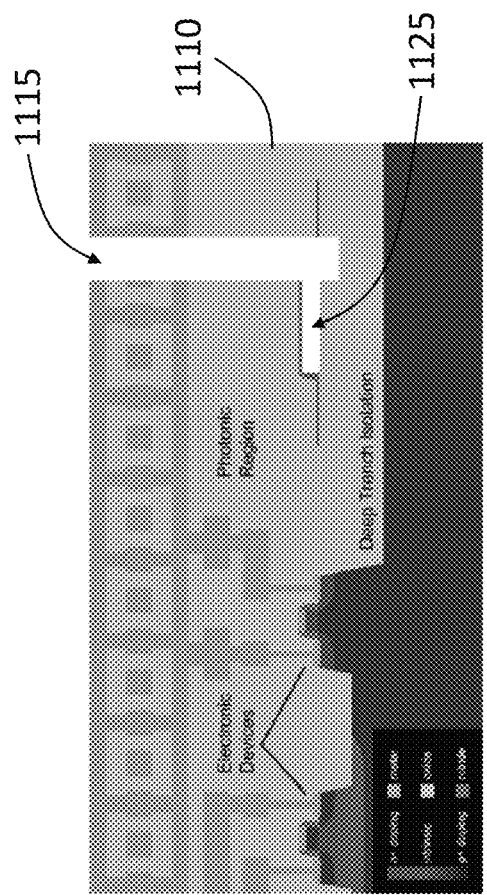
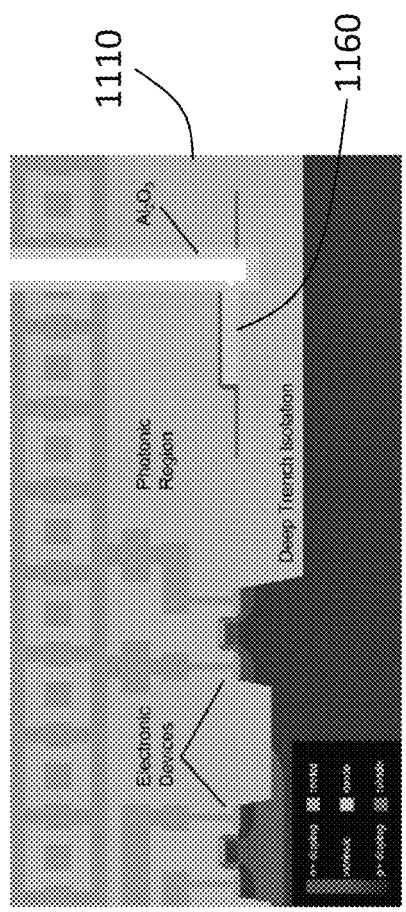
FIG. 11C
FIG. 11D

SYSTEMS AND METHODS FOR GENOME MAPPING

CROSS-REFERENCE TO RELATED APPLICATIONS

This application claims the priority benefit, under 35 U.S.C. § 119(e), of U.S. Provisional Patent Application No. 62/452,181, filed on Jan. 30, 2017, and entitled "NANOFLUIDICS AND WAVEGUIDE FOR VISIBLE LIGHT IN CMOS USING SACRIFICIAL LAYER WITH AN APPLICATION IN GENOME MAPPING." This application is incorporated herein by reference in its entirety.

GOVERNMENT SUPPORT

This invention was made with Government support under Grant No. ECCS-1408495 awarded by the National Science Foundation. The Government has certain rights in the invention.

BACKGROUND

The human genome includes 6 billion nucleotides strung into 23 chromosomes (diploid). Each strand of deoxyribonucleic acid (DNA) is, on average, 5 centimeters in length, where nucleotides are separated from each other by 0.34 nm and are stacked into a molecular helix having a width of about 2 nm. Contemporary engineering systems are now approaching the complexity and precision of the genome. For example, a processor today (e.g., the Nvidia GP102) includes about 12 billion transistors that occupy a space of approximately 2 cm×2 cm. The 16 nm complementary metal-oxide-semiconductor (CMOS) process used to fabricate such a chip has a critical dimension uniformity of 1.6 nm and supports a retail price of about $1,000 ($2/mm$^2$)—coincidentally equal to the cost of sequencing a human genome. The recent ability to engineer systems with comparable complexity and scale to biomolecules opens the door to a new generation of molecular tools. These applications range from DNA sequencing and mapping, to protein microarrays and sensors for metabolites.

In the last five years, there have been several commercial examples of silicon devices that take advantage of the precision, throughput, and cost of semiconductor manufacturing for molecular sensing. While the majority of third-generation DNA sequencing technologies rely on fluorescence sensing, the Ion Torrent instrument uses Ion Sensitive Transistors (ISFETs), integrated at the base of 1.25 micron microwells, to electrically sense changes in pH that are indicative of nucleotide integration on a DNA template. These chips are fabricated in a 110 nm CMOS process and have as many as 660 million sites of parallel microwells. The DNA template is introduced into the microwells on the surface as a bead. The DNA template length can be limited several factors, including: (a) steric hindrance limiting the density of binding sites when the DNA is long; and (b) dephasing (i.e., synthesis reactions falling out of step) that is common to sequence-by-synthesis approaches. Despite the relatively short DNA segments that are sequenced in the microwells, the massive parallelism still enables a high throughput and the manufacturing maturity of CMOS and on-chip electronic readout minimizes the instrument cost.

The short read length of the sequences represents a major challenge for whole genome sequencing. It is usually difficult to use simple alignment of short reads to a reference genome to investigate the full range of genomic variation. While overlapping sequence strings can be used to assemble these short read lengths (e.g., contigs), assembly into a larger scaffold often uses next-generation mapping, which can produce physical maps having unique sequence strings that can provide long-range structural information of the genome. However, the resolution of these mapping systems is usually 1500 base pairs (bp), an order of magnitude larger than the read length of high-performance sequencers. Hence, it is often challenging (e.g., if there are sequence repeats) to accurately assemble a whole genome sequence when no prior sequence information is available (i.e., de novo sequencing).

Optical readout and nanofluidics can support significantly longer read lengths and represents the state-of-the-art for next-generation genome mapping. For example, Pacific Biosciences is able to realize relatively long read lengths of about 10 kb to about 60 kb by introducing the DNA template in a solution and overcoming limitations in binding DNA templates to a microbead. The Pacific Biosences system uses a nanophotonic aperture to locally excite the fluorescently labelled nucleotide just before the incorporation during synthesis of a complementary DNA strand. As many as 150,000 parallel sites can be available, about 4,000 times smaller than the Ion Torrent CMOS chip, but the accuracy of these sequencers has been less satisfactory. Similarly, genome mapping systems utilizing nanofluidics and fluorescence imaging can map very long dsDNA (e.g., greater than 100 kb), but again the resolution is typically limited to only 1500 base pairs. This resolution is usually insufficient for sequencing, thereby limiting de novo assembly of the short sequences.

SUMMARY

Embodiments of the present technology generally relate to molecular mapping. In one example, a system for molecular mapping includes a semiconductor substrate defining a reservoir to receive a sample of molecules and a nanofluidic channel in fluid communication with the reservoir. The system also includes a plurality of electrodes, in electrical communication with the nanofluidic channel, to electrophoretically trap the sample of molecules in the nanofluidic channel. At least one avalanche photodiode is fabricated in the semiconductor substrate and disposed within an optical near-field of the nanofluidic channel to detect fluorescence emission from at least one molecule in the sample of molecules.

In another example, a method of molecular mapping includes loading a sample of molecules from a reservoir into a nanofluidic channel. The reservoir and the nanofluidic channel are defined within a semiconductor substrate. The method also includes trapping the sample of molecules in the nanofluidic channel at least in part with an electrophoretic force and detecting a fluorescence emission from at least one molecule in the sample of molecules using at least one avalanche photodiode fabricated in the semiconductor substrate and disposed within an optical near-field of the nanofluidic channel.

In yet another example, a method is directed to forming a nanofluidic channel in a substrate containing a buried sacrificial layer having a first end and a second end opposite the first end. The method includes anisotropically etching the substrate to expose a first portion of the buried sacrificial layer at the first end and expose a second portion of the buried sacrificial layer at the second end. The method also includes isotropically etching the first portion and the second portion of the buried sacrificial layer to form the nanofluidic channel.

In yet another example, a system for molecular mapping includes a semiconductor substrate defining a reservoir to receive a sample of molecules and a nanofluidic channel having a width substantially equal to or less than 100 nm and in fluid communication with the reservoir. A plurality of electrodes are in electrical communication with the nanofluidic channel to electrophoretically trap the sample of molecules in the nanofluidic channel. The system also includes at least one avalanche photodiode (120), fabricated in the semiconductor substrate and disposed within an optical near-field of the nanofluidic channel, to detect fluorescence emission from at least one molecule in the sample of molecules. The avalanche photodiode includes a p-n junction defining a plane and configured to receive the fluorescence emission along a direction substantially parallel to the plane of the p-n junction. The avalanche photodiode is also configured to detect the fluorescence emission with a resolution finer than a diffraction limit of the fluorescence emission.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 2A-2C show simulations of collection efficiency of the system shown in FIGS. 1A and 1B.

FIGS. 4A-4E illustrate a method of fabricating a nanofluidic channel that can be used in the system shown in FIGS. 1A and 1B.

FIGS. 5A-5C illustrate the propagation of the etch front during the fabrication of a nanofluidic channel using the method illustrated in FIGS. 4A-4E.

FIGS. 6A-6E are photographs of a chip including nanofluidic channels, electronics, and optoelectronics fabricated using a modified IBM 10LP (65 nm) bulk CMOS process in a 300 mm wafer facility.

FIGS. 10A and 10B show two closely spaced electrodes that can be used for dielectrophoretic trapping of particles in a nanofluidic channel.

FIGS. 11A-11D illustrate a method of fabricating a light waveguide that can be used in the system shown in FIGS. 1A and 1B for guiding visible light.

DETAILED DESCRIPTION

Systems for Genome Mapping

Figure 1A:
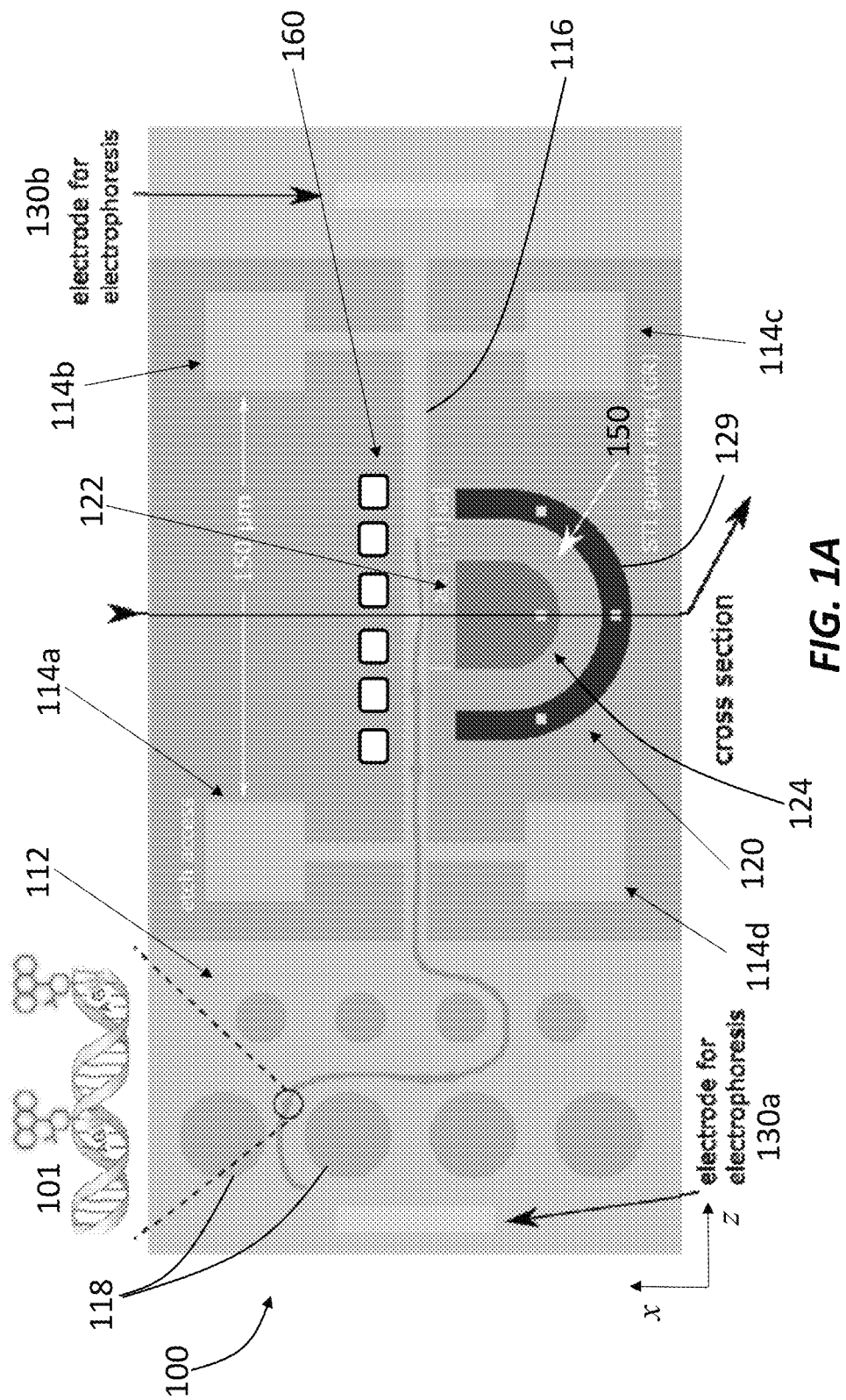
FIGS. 1A and 1B show a top view and a cross-sectional view, respectively, of a system for genome mapping based on near-field imaging of molecules in a nanofluidic channel.

To address the drawbacks in conventional genome mapping, systems and methods described herein leverage the precision and scale of complementary metal-oxide-semiconductor (CMOS) technology to integrate nanofluidics, nanophotonics, and nanoelectronics into the same platform. In general, nanofluidics can accurately place molecules within the sensing region, nanophotonics can provide high-resolution and fast on-chip readout, and nanoelectronics can stabilize the location of the molecules and accordingly improve the spatial resolution of the sensing. Within the context of DNA sequencing and mapping, nanofluidics can be used to elongate the DNA and to position the molecules within the near field of single-photon detectors. Integrated electronics read the detector signal and precisely control the locations of the individual fluorophores. Monolithic integration can also improve the resolution of fluorescent genome mapping (e.g., to about 150 bp, or equivalent to about 50 nm) while at the same time increase the scale of parallel reads to above 100,000 and reduce the overall instrument size and cost with on-chip readout.

Nanofluidics, nanophotonics, and nanoelectronics that are involved in genome mapping can be implemented within fully electronics-capable CMOS processes. Existing CMOS devices include, for example, low-loss waveguides, grating couplers for coupling between optical fibers and external optics (e.g., microscopes and lenses), micro-resonators for filters and modulators, detectors (e.g., based on Silicon, SiGe, and defect states in polysilicon), and thermal tuning for resonant devices. These functions can be implemented monolithically within state-of-the-art CMOS foundries, allowing integration with electronic circuitry to realized improved functions without extensive modifications of existing technologies.

The technology used to implement CMOS photonic platforms, such as high-voltage electrodes and photon counting visible detectors within the Global Foundries/IBM 90 bulk CMOS platform, can also be used to make integrated genome mapping systems. These integrated genome mapping systems may be made of a greater variety of materials and have a broader span of dimensions and functions compared to conventional CMOS photonics devices. Nevertheless, the simulation and design tools used to design and fabricate planar integrated optical devices can be adapted to design and fabricate integrated optical and electronic devices for genome mapping.

As described herein, a high-resolution, high-throughput genome mapping system can include sub-100 nm nanofluidic channel arrays, single-molecule sensitive photodetectors with high collection efficiency, and electrophoretic control over the motion of the molecules. DNA is extended in nanofluidic channels and visualized by fluorescence microscopy, revealing the DNA contour decorated with a pattern of fluorescent spots. To elongate the DNA, the nanofluidic channels (also referred to as nanochannels herein) have dimensions on the order of the persistence length (i.e., the length over which a polymer behaves as a rigid rod) of about 50 nm.

In addition, these nanofluidic channels are disposed within the near field of the photon-counting detectors to address at least two challenges in conventional mapping systems. First, near-field imaging can overcome the diffraction limit that limits the spatial resolution of conventional far-field fluorescence imaging (e.g., using a microscope). Second, the close proximity between the nanofludic channels and the detector can also improve the collection efficiency. The electrophoretic control over the motion of the molecules is realized by electrodes disposed on or near the nanofluidic channels.

Figure 1B:
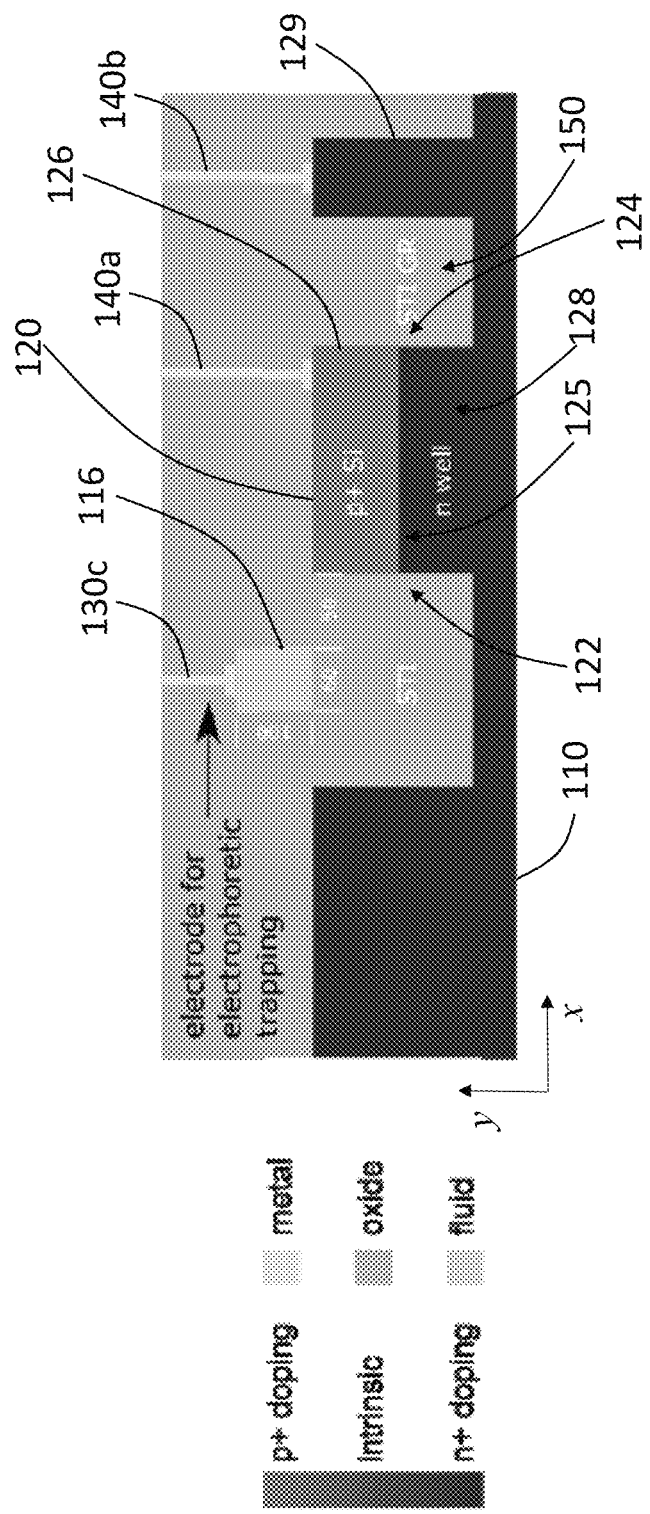

FIGS. 1A and 1B show a top view and a cross sectional view, respectively, of a system 100 for genome mapping based on near-field imaging of molecules in a nanofluidic channel 116 (also referred to as nanochannel 116). The system 100 includes a substrate 110 (e.g., a silicon substrate) that defines a reservoir 112 to receive a sample of molecules 101. Multiple nano-pillars 118 (e.g., silicon oxide pillars) are formed in the reservoir 112 to help molecules (e.g., DNA molecules) stretch out to a linear form. The nanofludic channel 116 is in fluidic communication with to the reservoir 112 to flow the molecules 101. The substrate 110 also defines multiple etching access regions 114a, 114b, 114c, and 114d (collectively referred to as etching access regions 114) that are used to fabricate the nanofludic channel 116 (more details are provided below with reference to FIGS. 5A-5E). A pair of electrodes 130a and 130b are disposed on the two ends of the nanofludic channel 116 to facilitate the loading of the molecules 101 from the reservoir 112 into the nanofludic channel 116 via electrophoresis force and/or electroosmosis.

An avalanche photodiode (APD) 120 is fabricated in the substrate 110 near the nanofluidic channel 116 to detect fluorescence emission from the molecules 101. The APD 120 can be within the optical near field of the nanofluidic channel 116 (or the optical near field of the sample of molecules 101 in the nanofluidic channel 116). Without being bound by any particular theory of mode operation, the optical near field can be defined as the area within a threshold distance from the nanofluidic channel 116 (or the optical near field of the sample of molecules 101 in the nanofluidic channel 116). The threshold distance can be substantially equal to or less than the wavelength of the fluorescence emission, which can be about 300 nm to about 800 nm. The distance between the APD 120 and the nanofluidic channel 116 can be about 50 nm to about 300 nm (e.g., about 50 nm, about 100 nm, about 150 nm, about 200 nm, about 250 nm, or about 300 nm, including any values and sub ranges in between).

As illustrated in FIG. 1B, the avalanche photodiode 120 has a front surface 122 and a back surface 124 opposite the front surface 122. The front surface 122 is towards the nanofludic channel 116 and receives the fluorescence emission. In some examples, the front surface 122 is flat, while the back surface 124 is curved to reduce the electric field at the edge of the avalanche photodiode 120 (see, FIG. 1B).

The APD 120 also includes a p-doped region 126, an n-doped region 128 (e.g., N well in the substrate 110), and a p-n junction 125 between the p-doped region 126 and the n-doped region 128. The p-n junction 125 can be substantially parallel to the plane of the substrate 110 (or the flow direction of the sample of molecules 101 in the nanofluidic channel 116), and photons of fluorescence emission from the sample of molecules 101 in the nanofluidic channel 116 can be coupled into the APD 120 from the front surface 122. This configuration can increase the detection efficiency of the APD 120.

As illustrated in FIG. 1B, the system 100 also includes a second p-doped region 129 (e.g., defined by the substrate 110), which is disposed around the back surface 124 of the APD 120. A shallow trench isolation (STI) is formed between the APD 120 and the second p-doped region 129 and filled with an oxide to form a guard ring 150 that can reduce the probability of premature breakdown in the APD 120. The width of the guard ring 150 (i.e., the distance between the back surface 124 of the APD and the second p-doped region 129) can be about 50 nm to about 300 nm (e.g., about 50 nm, about 100 nm, about 150 nm, about 200 nm, about 250 nm, or about 300 nm, including any values and sub ranges in between). A first set of electrodes 140a is disposed on the p-doped region 126 and a second set of electrodes 140b is disposed on the second p-doped region 129 to operate the APD 120. For example, the electrodes 140a and 140b can bias the APD for Geiger-mode operation (i.e., photon counting operation).

The system 100 can include one or more additional electrodes 130c to trap the sample of molecules 101 within the nanofluidic channel 116 and/or reduce the flow speed of the sample of molecules 101 so as to facilitate imaging. For example, the additional electrode(s) 130c can be disposed on the nanofluidic channel 116. Only one electrode 130c is illustrated in FIGS. 1A and 1B, but multiple electrodes can be employed as well (e.g., distributed along the nanofluidic channel 116).

In some examples, the width of the nanofludic channel 116 (i.e., the dimension along the x direction as illustrated in FIG. 1A) can be on the order of the persistence length of a DNA, which is usually about 50 nm. For example, the width of the nanofluidic channel 116 can be about 100 nm or less (e.g., about 100 nm, about 90 nm, about 80 nm, about 70 nm, about 60 nm, about 50 nm, or less, including any values and sub ranges in between). The height of the nanofludic channel 116 (i.e., the dimension along they direction as illustrated in FIG. 1B) can also be about be about 100 nm or less (e.g., about 100 nm, about 90 nm, about 80 nm, about 70 nm, about 60 nm, about 50 nm, or less, including any values and sub ranges in between). In one example, the width can be substantially equal to the height. In another example, the width can be different from the height (e.g., the height can be greater than the width, as shown in FIG. 1B). The length of the nanofluidic channel 116 (i.e., the dimension along the z direction as illustrated in FIG. 1A) can be substantially equal to or greater than 100 µm (e.g. about 100 µm, about 120 µm, about 150 µm, about 200 µm, about 300 µm, about 500 µm, or longer, including any values and sub ranges in between).

In FIGS. 1A and 1B, the p-doped region 126 of the APD 120 is disposed on the n-doped region 128. This doping configuration can be reversed. For example, the APD 120 can include an n-doped region disposed on a p-doped region formed of a p well within the substrate 110. In addition, other types of detectors that are compatible with CMOS processes can also be used to detect the fluorescence emission from the sample of molecules 101.

FIGS. 1A and 1B show the system 100 with a single APD 120 to detect the fluorescence emission from the sample of molecules 101. In another example, the system 100 can include multiple detectors 160 disposed along the nanofluidic channel 116 (i.e., along the flow path of the sample of molecules 101) to increase the signal-to-noise ratio (SNR) of the detection. In one example, the detectors 160 can be disposed on the same side of the nanofludic channel 116 (as illustrated in FIG. 1A). In another example, the detectors 160 can be disposed on both sides of the nanofluidic channel 116.

In one example, the electrodes 130a, 130b, and 130c (collectively referred to as electrodes 130) can be configured to apply a direct current (DC) voltage to the nanofluidic channel 116 for electrophoretic trapping. In another example, the electrodes 130 can be configured to apply an alternate current (AC) voltage to the nanofluidic channel 116 so as to trap the sample of molecules 101 via dielectrophoretic force. The electrophoretic or dielectrophoretic force can also suppress Brownian motion of the molecules 101, thereby improving the imaging quality for the APD 120. To facilitate trapping, some electrodes (e.g., electrode 130c) can be disposed close to the APD 120. For example, the distance between the electrode 130c and the APD 120 can be about 10 µm or less (e.g., about 10 µm, about 5 µm, about 3 µm, about 2 µm, about 1 µm, about 500 nm, or less, including any values and sub ranges in between).

High Resolution for High-Throughput Genome Mapping

As described above, the resolution for existing DNA mapping tools is usually limited by two factors: 1) the diffraction limit in far field imaging (e.g., using a microscope); and 2) the Brownian motion of the molecule in solution, which can cause blurring in the resulting image. Diffraction-limited optical imaging restricts the ability to resolve two adjacent fluorophores that are closer than about half the detected wavelength. For example, at a wavelength of 500 nm, the corresponding diffraction limit is approximately 250 nm, equivalent to about 735 basic pairs (bp). In general, two strands of DNA are held together in the shape of a double helix by the bonds between base pairs. The number of base pairs (bp) is often used as a measure of length of a DNA segment. However, since the DNA molecules remain suspended in solution inside the channels, they usually undergo thermal fluctuations within the duration of a single imaging exposure. Consequently, the current state of the art platform can resolve labels separated by about 1500 bp.

There are several approaches to overcome the diffraction limit of conventional far-field microscopy. Out of these approaches, super-resolution localization of labelled sequences for genome mapping can be used to localize labels with an accuracy of about 300 bp. This approach includes fitting a Gaussian distribution to each isolated fluorophore (e.g., molecule) and tracking the fluctuating motion of its centroid. The fitting and tracking of the point spread function (PSF) usually involve high collection efficiency (high SNR). The system 100 shown in FIGS. 1A and 1B achieves high collection efficiency using nanofluidics and near-field detection. This high collection efficiency, combined with the narrow PSF (e.g., about 200 nm) of each fluorophore and capturing of multiple exposures of the fluorophore, can yield a resolution better than 50 nm (equivalent to about 150 bp).

FIGS. 2A-2C illustrate how the system 100 of FIGS. 1A and 1B operates with resolution better than 50 nm. FIG. 2A shows the imaging section of the system 100. The APD 120 is disposed within the optical near field of the nanofluidic channel 116, in which the sample of molecules 101 is flowing. FIG. 2B shows calculated collection efficiency as a function of the location of the sample of molecules 101. The location is measured in terms of the offset from the location of the APD 120. The calculation was carried out using a finite-difference time-domain (FDTD) simulation. FIG. 2C shows an optical intensity profile of x-polarized dipole source in the imaging section shown in FIG. 2A.

In this simulation, the nanofludic channel 116 is placed about 50 nm from the APD 120. The molecule 101 is simulated as a dipole optical source, which is placed at the near corner of the nanofluidic channel 116 to the APD 120. The wavelength of the dipole source is set as 500 nm, which is a common wavelength for fluorescence emission. The output of the source has an optical bandwidth of about 30 nm. The fraction of the light coupled into the APD 120 is calculated by dividing the optical flux into the silicon from the total flux exiting the dipole source. The longitudinal width of the p+ doped region is set as about 200 nm. The FDTD simulation is performed for all three polarization of the dipole and an average value is calculated.

As shown in FIG. 2B, the collection efficiency of the SPD 220 while the dipole is near the center of the APD 120 (zero offset) is about 30%. As the dipole moves away from the center of the p+ doped region to a position about 200 nm away, the collection efficiency drops to below 10%. The relative position of the fluorophore can be calculated from the photocount signal. Multiple detectors can be placed along the nanofluidic channel 116 for repetitive detection and further SNR enhancement.

Photon-Counting Detectors in CMOS

Fabricating the APD 120 in a CMOS process can have several advantages. For example, the CMOS process allows integration of the read-out electronics, thereby enabling scaling of the number of qubits as well as local processing of the state information. In addition, the CMOS process also has good reproducibility of the APD's dark current and gain characteristics. Furthermore, the CMOS process can lead to low dark currents due to the high quality of the materials and processes used in state-of-the-art CMOS.

Figures 3A, 3B:
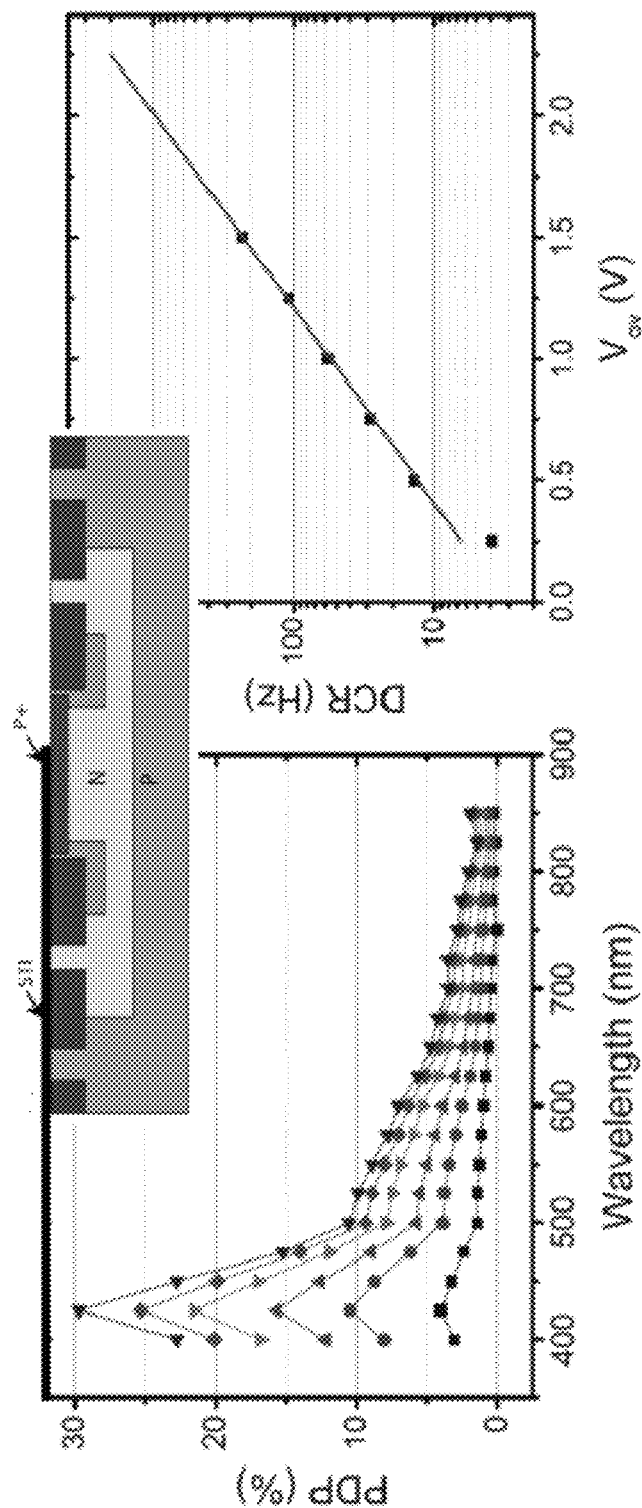
FIG. 3A shows measured photon detection probability (PDP) of a CMOS avalanche photodiode (APD) as a function of wavelength.
FIG. 3B shows measured dark count rate (DCR) of a CMOS APD versus the over-voltage.

FIG. 3A shows measured photon detection probability (PDP) of an avalanche photodiode (APD) (shown in the inset) as a function of wavelength for various voltages in excess of the breakdown voltage (defined as over-voltage $V_{ov}$) by between 0.25 and 1.5 V. FIG. 3B shows the measured dark count rate (DCR) of the APD versus the over-voltage. The APD was fabricated in the IBM 130 nm bulk CMOS foundry. The PDP was approximately 30% at 426 nm and the DCR was about 231 per second at a total applied voltage of 13.6 volts for a 5-µm device. The quantum efficiency or PDP for this vertically illuminated device may be limited by the shallow junctions in this CMOS process. Accordingly, the PDP is typically greater for blue photons. The PDP can be increased significantly by coupling light into the detector from the side (e.g., parallel or nearly parallel to the p-n junction 125 in FIG. 1A). In addition, the field terminations can be configured to suppress premature breakdown and to ensure that nearly all of the photons coupled into the silicon generate electron-hole pairs. For example, as illustrated in FIGS. 1A and 1B, one set of electrodes 140a is disposed on the p-doped region 126 and a second set of electrodes 140b is disposed on the second n-doped region 129 surrounding the back surface 124 of the APD 120.

Near-field coupling between the nanochannel-bound fluorophore and the silicon APD fabricated in CMOS can increase the collection efficiency of photons. One constraint, however, is that the excitation light for exciting the fluorescence emission may also enter the APD via scattering. To address this issue, the APD bias can be synchronized with the excitation laser pulse. This time gating can be used to "blind" the detector from the excitation light for less than 1 ns. For example, the timing of the excitation laser pulse can be recorded, and the time range within which the fluorescence emission might arrive at the APD 120 can be estimated. Accordingly, the APD can be turned on during this time range and blinded in other times.

Methods of Fabricating Nanofluidic Channels

The precisely placed nanofludic channel 116 in the system 100 can be fabricated alongside the APD 120 and associated electronics on a CMOS platform, such as the IBM 65 nm bulk CMOS platform. During fabrication, gate polysilicon can be used as a sacrificial layer to pattern the nanofluidic channel 116. Reactive ion etching can be used to drill vertical access holes from the top surface of the substrate to expose the polysilicon, which can then be removed by a highly selective $XeF_2$ etch.

Figures 4A, 4B:
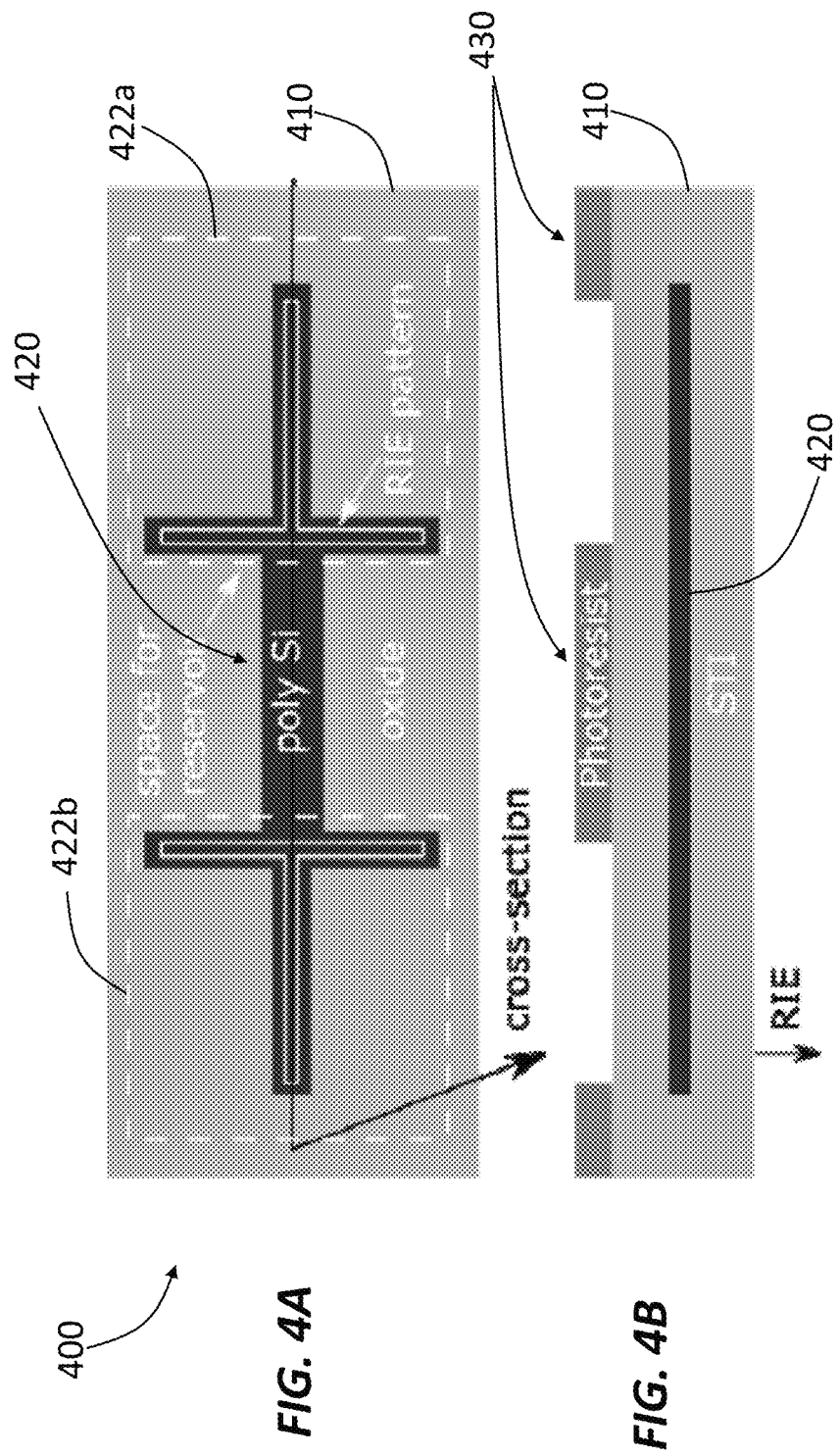

FIGS. 4A-4E illustrate a method 400 of fabricating a nanofluidic channel that can be used in the system 100. The method 400 starts with a substrate 410 embedded with a sacrificial layer 420 (e.g., a crystal silicon body layer or gate polysilicon layer) as shown in FIG. 4A. The sacrificial layer 420 has two ends 422a and 422b each having a T-shape. FIG. 4B shows a side view of the substrate 410. FIG. 4B also shows that a coarse photomask 430 is placed on the substrate 410. The photomask 430 is used to pattern vertical access holes 412a and 412b (collectively referred to as access holes 412) on both ends of the sacrificial layer 420 as shown in FIG. 4C. The two access holes 412 also define the ends of the nanofluidic channel to be fabricated subsequently.

Since the sacrificial layer 420 has two T-shaped ends 422a and 422b. the resulting access holes 412 may also have a T-shape, which can facilitate alignment between conventional PDMS microfluidic reservoirs and the CMOS chip including the nanofluidic channel. A simple large opening in the polysilicon pattern may violate CMOS process rules for fill density. Reactive ion etching (ME) is used for anisotropic etching through the substrate 410 (including silicon dioxide) and any inter-metal dielectrics on top of the sacrificial layer 420. Afterwards, an $XeF_2$ etch is used to selectively remove the sacrificial layer 420 so as to form a nanofluidic channel 422 and accordingly a nanofludic chip 450 as shown in FIG. 4D. The dimensions of the nanofluidic channel 422 can be substantially similar to the nanofluidic channel 116 shown in FIGS. 1A and 1B.

In FIG. 4E, a microfluidic chip 440 (e.g., made of polydimethylsiloxane or PDMS) is coupled to the nanofluidic chip 450. The microfluidic chip 440 can include two channels 442a and 442b that are aligned with the access holes 412. In operation, the microfluidic chip 440 can be used to provide the sample of molecules for the nanofludic chip 450.

FIGS. 5A-5C illustrate the propagation of the etch front during the fabrication of a nanofluidic channel using the method illustrated in FIGS. 4A-4E. The $XeF_2$ etching process used for etching the sacrificial layer 420 is usually isotropic and highly selective, thereby allowing lateral etching of high aspect ratio channels. As used herein, the aspect ratio of a nanofluidic channel refers to the ratio of the channel length to the channel height (illustrated in FIGS. 1A and 1B). In some examples, the fabrication can be configured to produce nanofluidic channels having an aspect ratio greater than 100 (e.g., about 100, about 200, about 500, about 1000, about 1500, about 2000, about 3000, about 5000, or greater, including any values and sub ranges in between). In addition, all reactants in the method 400 can be neutral species in a gas phase, thereby allowing rapid diffusion. As seen in FIGS. 5A-5C, an etch length of about 93 µm is demonstrated with a channel height of about 100 nm, and the channel is formed with only 110 cycles of 20 s etching.

FIGS. 6A-6E show photographs of a chip including nanofluidic channels, electronics, and optoelectronics fabricated using a modified IBM 10LP (65 nm) bulk CMOS process in a 300 mm wafer facility. FIG. 6A is a photograph of the entire chip and FIG. 6B shows one die on the chip having a size of about 31×26 mm. FIGS. 6C and 6D illustrate an array of nanofludic channels and FIG. 6E shows the structure of a single nanofluidic channel. In addition to the nanofluidic test structure, the die also contains electronic and active optoelectronic structures, such as a depletion-based infrared modulator. In FIG. 6D, devices are drawn with Virtuoso Cadence. All layouts are generated automatically by codes called parameterized cells. They are designed to facilitate easy repetition and variation of parameters. In addition to patterning the sacrificial polysilicon, extra masks can be used to shape shallow trench isolation, doping profile, and fill shapes. The fabrication is achieved without major design rule waivers.

Figures 7A, 7B:
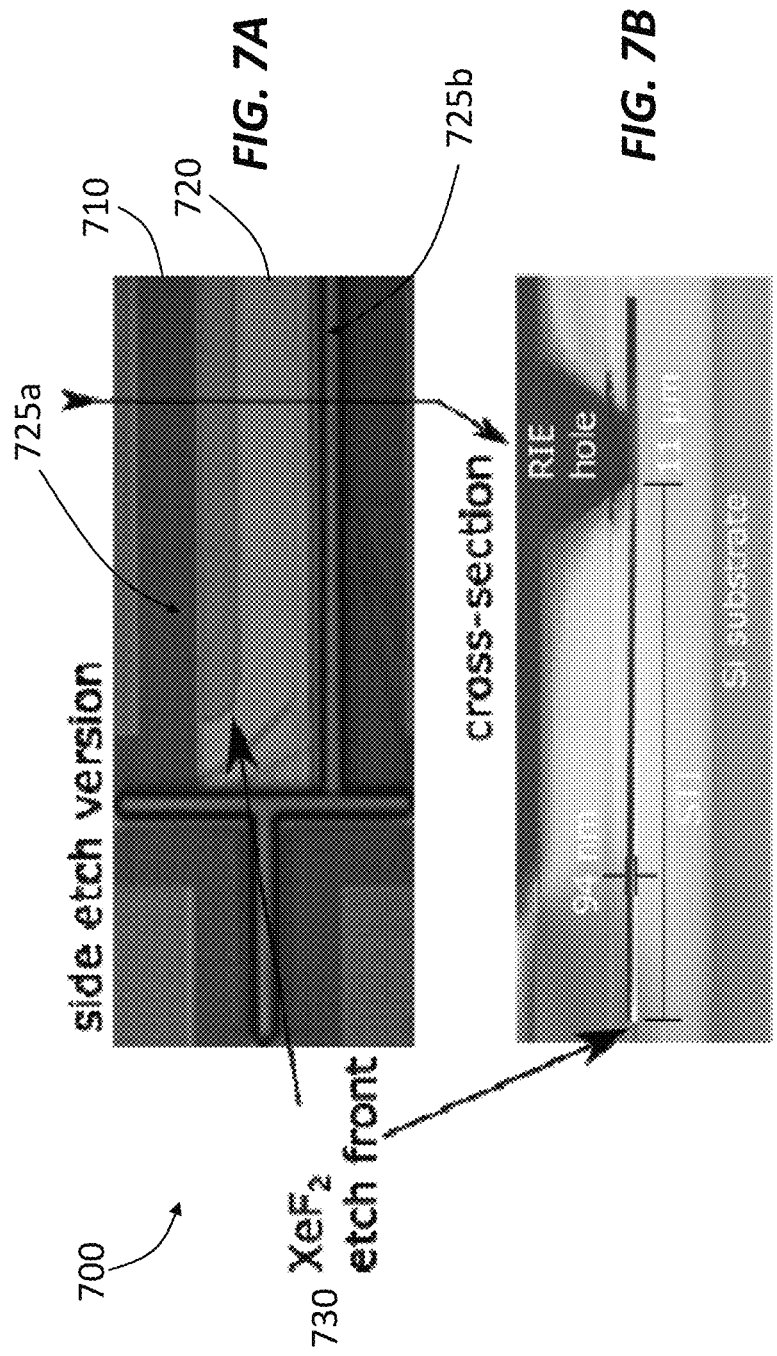
FIGS. 7A and 7B illustrate a method of fabricating a nanofluidic channel via side etching.

FIGS. 7A and 7B illustrate a method 700 of fabricating a nanofluidic channel by side etching. In this method, a sacrificial layer 720 (e.g., gate polysilicon) is embedded in a substrate 710 (e.g., silicon oxide) as shown in FIG. 7A. The sacrificial layer 720 has a side section 725a that can be exposed to for etching using a corresponding photomask having a slit along the side section 725a. FIG. 7A also shows the $XeF_2$ etch front 730 that can propagate from the side section 725a toward the opposite side 725b, thereby forming a nanofluidic channel.

The etching can start from both sides 725a and 725b to increase the efficiency. In addition, the method 700 can be combined with the method 400 illustrated in FIGS. 4A-4E. In this instance, the sacrificial layer can be etched along the length and along the width.

FIG. 7B is a scanning electron microscope (SEM) image of the cross-section of the nanofluidic channel illustrated in FIG. 7A. The etched channel has a depth of about 11 µm from the side section 725*a* toward the opposite side 725*b* and a height of about 100 nm, which can translate to an aspect ratio greater than 100.

Figure 8:
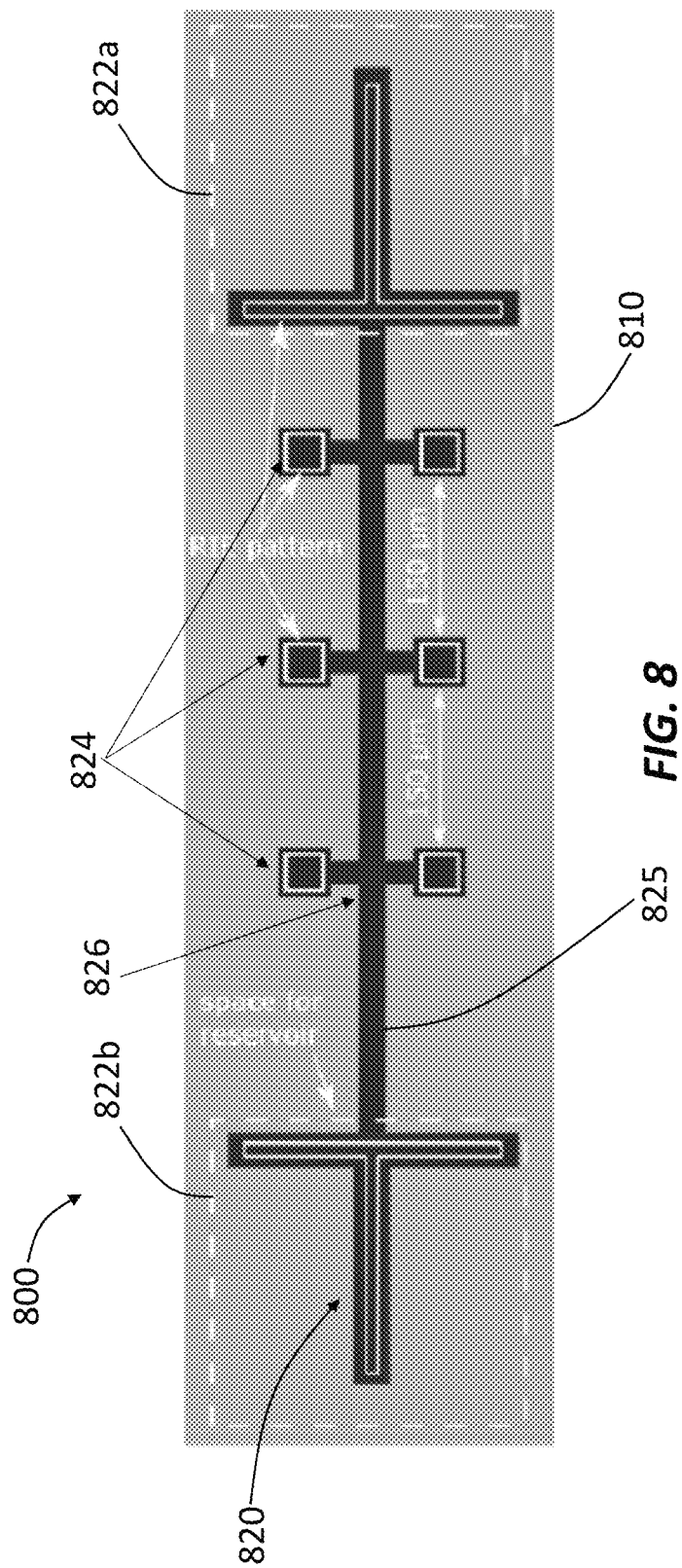
FIG. 8 illustrates a method of fabricating a nanofluidic channel longer than 100 μm.

FIG. 8 illustrates a method 800 of fabricating a nanofluidic channel having a length greater than about 100 µm. The method 800 uses a sacrificial layer 820 (e.g., polysilicon) embedded within a substrate 810. The sacrificial layer 820 includes two end sections 822*a* and 822*b* (collectively referred to as end sections 822) that can be used to define reservoirs (e.g., reservoir 112 in FIG. 1A). The sacrificial layer 820 also includes multiple side etch accesses 824 disposed along a channel section 825. The side etch accesses 824 can be used to allow etching the channel section 825, which defines the nanofluidic channel, from locations in the middle of the channel section 825 (e.g., location 826). The distance between adjacent side accesses 824 can be, for example, less than about 150 µm, so that any section of sacrificial layer 820 is within about 100 µm from at least one access point.

Figures 9A, 9B, 9C:
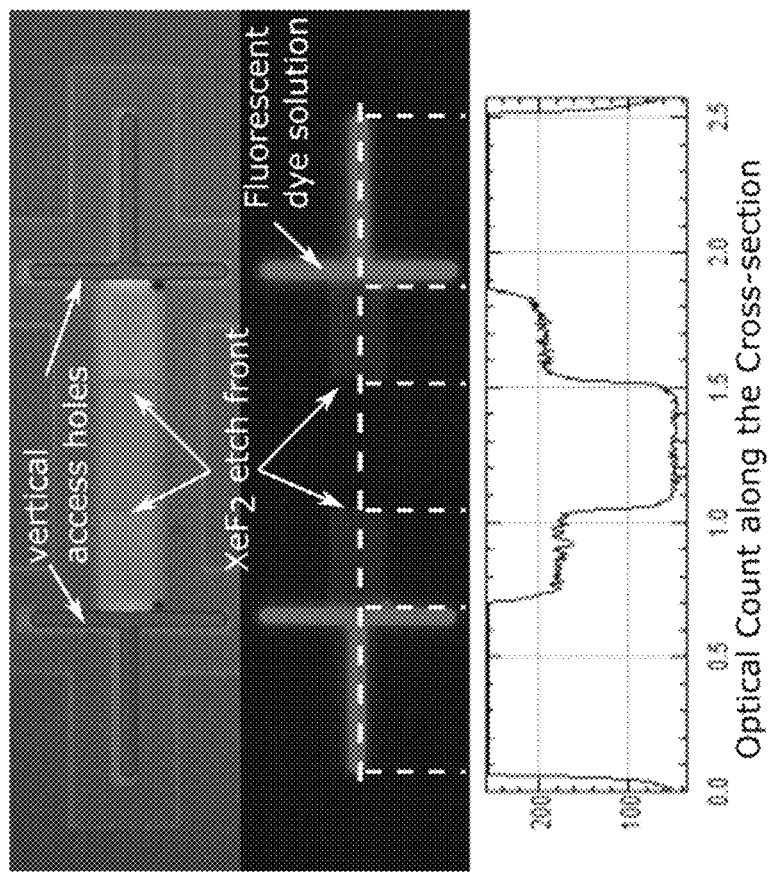
FIGS. 9A-9C illustrate the wettability of a nanofludic channel fabricated using the method illustrated in FIGS. 4A-4E.

FIGS. 9A-9C illustrate the wettability of a nanofludic channel fabricated using the method illustrated in FIGS. 4A-4E. FIG. 9A shows an image of the nanofluidic channel. The middle of the corresponding sacrificial layer is not etched to highlight the wettability of the etched sections. The nanofluidic channel is loaded with a water-based fluorescent solution. FIG. 9B shows that the etched sections (two ends near the vertical access holes) emit visible fluorescence emission. FIG. 9C shows the distribution of photon counts from fluorescence along the nanofluidic channel. The photon counts from the etched sections are significantly higher than the photons count from the middle section (oxide background). FIGS. 9A-9C demonstrate that the liquid solution successfully wets the nanofluidic channel.

CMOS Dielectrophoretic Traps

Systems described herein, including the system 100 in FIGS. 1A and 1B, allow a molecule to be placed in close proximity (e.g., within 50 nm) of a silicon photon-counting APD. The high collection efficiency (e.g., 30%) and high sensitivity (photon counting) lead to high SNR measurements of the fluorophore while it moves within the nanofluidic channel. Because the DNA molecule is suspended in solution, the fluorophore typically experiences thermal fluctuations that cause constant changes of the fluorophore positions. This Brownian motion may affect both the sensitivity of the detection (e.g. by changing the near-field distance to the detector) and the lateral spatial resolution. These effects can be addressed, at least partially, by dielectrophoretic trapping structures, which are also compatible with the CMOS process that can be used to fabricate the system 100.

As described above, electrophoresis can be used to load the sample of molecules (e.g., DNA molecules) into the nanofluidic channel. This can be accomplished by applying direct current (DC) voltage across the length of the nanofluidic channel. The resulting electrophoretic force can pull the negatively charged phosphate groups within the DNA. After the DNA is loaded into the nanofluidic channel, this DC voltage can be reduced so that the labelled DNA is slowly pulled through the nanofludic channel and passed over the APD or APD array.

The negative charges in the DNA can also attract a cloud of mobile ions from the surrounding solution. This solvation cloud, in turn, can result in a high polarizability for the DNA and allow dielectrophoretic trapping in an alternating current (AC) electric field gradient. A large electric field gradient can be used to trap particles and suppress Brownian motion. Without being bound by any particular theory or mode of operation, the smallest size at which a spherical particle may be trapped stably in a field gradient can be calculated as $$r > \left(\frac{10kT}{\pi\varepsilon_m \Delta d \mathrm{Re}[K(\omega)]\nabla E^2}\right)^{1/3} \quad (1)$$

where $\varepsilon_m$ is the dielectric permittivity of the solution, $\Delta d$ is the electrode spacing (over which the gradient is approximately constant), K is Clausius-Mossotti factor for molecular polarizability, and $\nabla E^2$ is the field gradient.

In some examples, the distance between electrodes (e.g., electrodes 130*c*) can be about 2 µm to about 4 µm. The resulting field gradient is about $1-2 \times 10^{17}$ V²/m³. According to Equation (1), this gives a minimum radius for a stably trapped particle of about 33 nm. In systems described herein, the field gradient can be even greater as the electrode spacing can be as small as 100 nm.

FIGS. 10A and 10B show two closely spaced electrodes that can be used for dielectrophoretic trapping of particles in a nanofluidic channel. The two electrodes in FIG. 10A are about 500 nm from each other. Accordingly, they can be used to trap single protein molecules with voltages as low as 10 V oscillating at 1 MHz. In operation, DNA is usually constrained by its length so that thermal fluctuations do not scatter the fluorophore's positions as much as for an untethered sphere (as used in Equation (1)). The effective size of the DNA is greater than the persistence length (e.g., about 50 nm) and therefore it can be easier to stably trap DNA and suppress its Brownian motion than to trap untethered spheres. In addition, dielectrophoretic trapping can be entirely reversible, thereby imposing no restriction on the movement of the DNA when the AC field is turned off Methods of Fabricating Optical Waveguides for Fluorescence Excitation In systems described herein (e.g., system 100 in FIGS. 1A and 1B), the fluorescence emission from the sample of molecules can be excited by one or more beams of excitation light. In some examples, the excitation light beams can be provided by an external light source, such as a laser. In some other examples, the excitation light beams can be provided by a light source integrated with the imaging system (e.g., a semiconductor laser fabricated in the substrate 110). In either case, light waveguides can be used to guide the excitation light beams from the light source to the nanofludic channel to excite the sample of molecules within the nanofludic channel. In addition, these light waveguides can also be used to guide the visible fluorescence emission for further analysis.

Figures 11A, 11B:
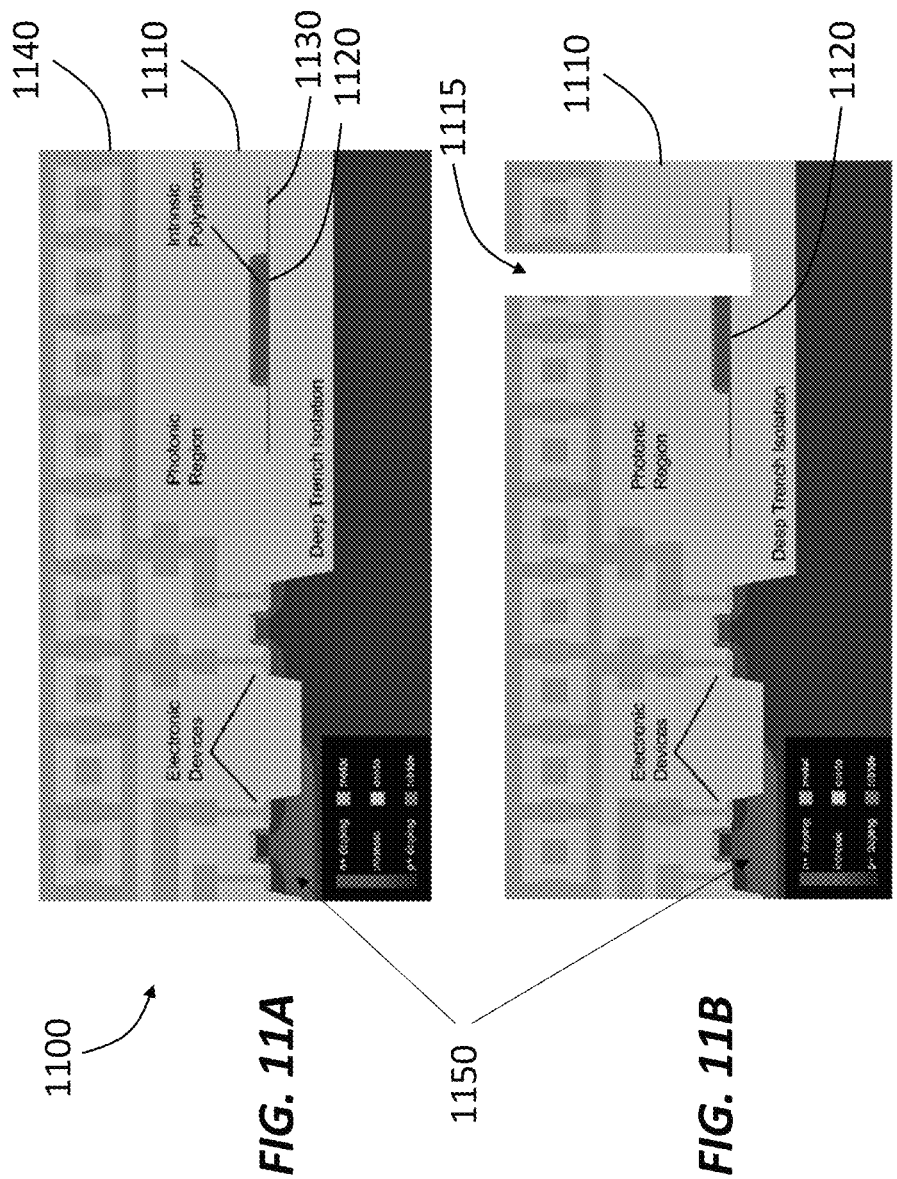

FIGS. 11A-11D illustrate a method 1100 of fabricating an optical waveguide in a CMOS platform for guiding visible light. FIG. 11A shows a side view of bulk CMOS chip 1110 with fabricated electronic devices 1150 (e.g., transistors). The chip 1110 may have a metal layer 1140 disposed on the top. A sacrificial layer 1120 (e.g., including materials for transistor gates, such as polysilicon) is disposed within the chip 1110. A nitride layer 1130 is disposed on the sacrificial layer 1120 and within the chip 1110.

In FIG. 11B, a vertical access hole 1115 is created in the chip 1110 by anisotropic etching, such as RIE. The vertical access hole 1115 exposes at least one end of the sacrificial layer 1120 for further processing. In FIG. 11C, XeF₂ etching is used to isotropically etch away the sacrificial layer 1120 and form a channel 1125 (also referred to as a void 1125). In FIG. 11D, the channel 1125 is filled with a dielectric material to form an optical waveguide 1160. The filling can be carried out via, for example, atomic layer deposition (ALD). The dielectric material can have a refractive index greater than the refractive index of the chip 1110. Examples of suitable dielectric material include aluminum oxide ($Al_2O_3$), aluminum nitride (AlN), hafnium oxide ($HfO_2$), titanium oxide ($TiO_2$), silicon oxide ($SiO_2$), and tungsten nitride (TiN).

Figure 12A:
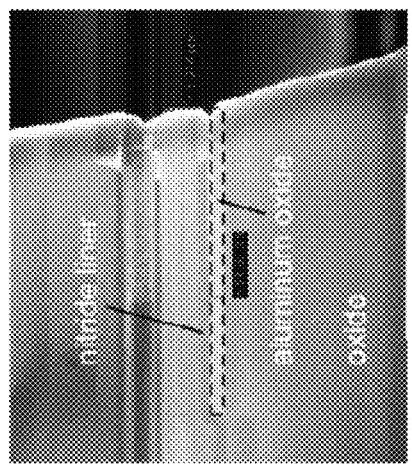
FIGS. 12A-12C show SEM images of a photoresist, a channel, and a light waveguide, respectively, during the fabrication method illustrated in FIGS. 11A-11D.
Figure 12C:
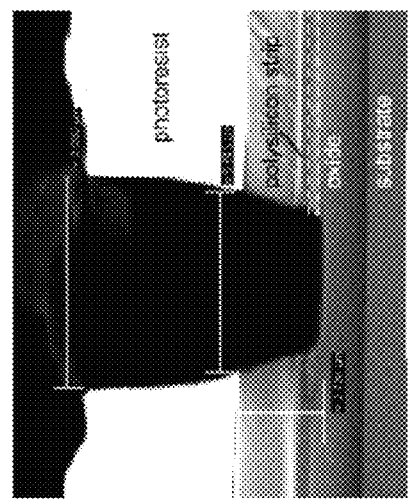
Figure 12B:
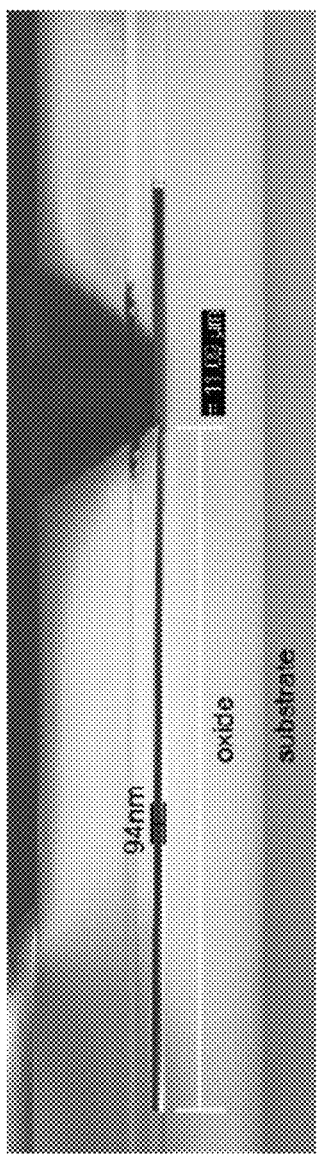

FIG. 12A shows an SEM image of a photoresist (e.g., AZ4620) that can be used to pattern the vertical access hole 1115 in the method 1110. FIG. 12B shows an SEM image of a channel (e.g., channel 1125 in FIG. 11C) formed after etching away the sacrificial layer 1120 in the method 1100. The channel has a length greater than 11 μm and a height of about 94 nm. The corresponding aspect ratio is greater than 100. And FIG. 12C shows an SEM image of the optical waveguide (e.g., optical waveguide 1160 in FIG. 11D) including aluminum oxide deposited via ALD. The optical waveguide has an aspect ratio greater than 20.

Figure 13A:
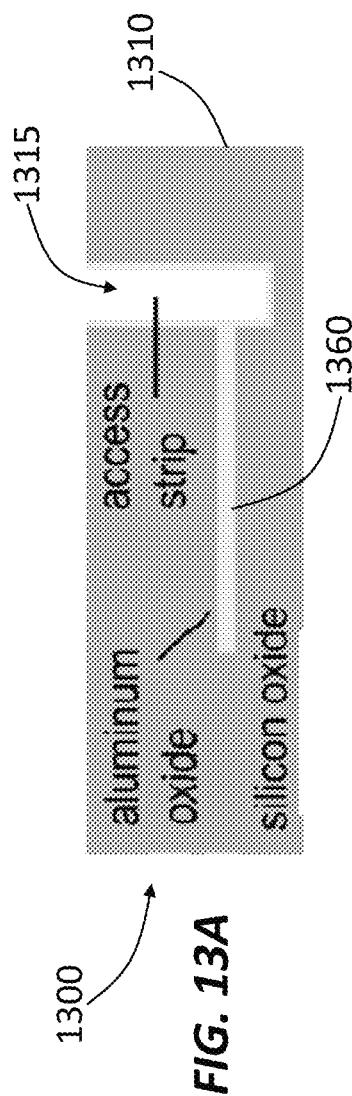
FIGS. 13A-13C illustrate light guiding in a light waveguide fabricated using the method illustrated in FIGS. 11A-11D.
Figure 13B:
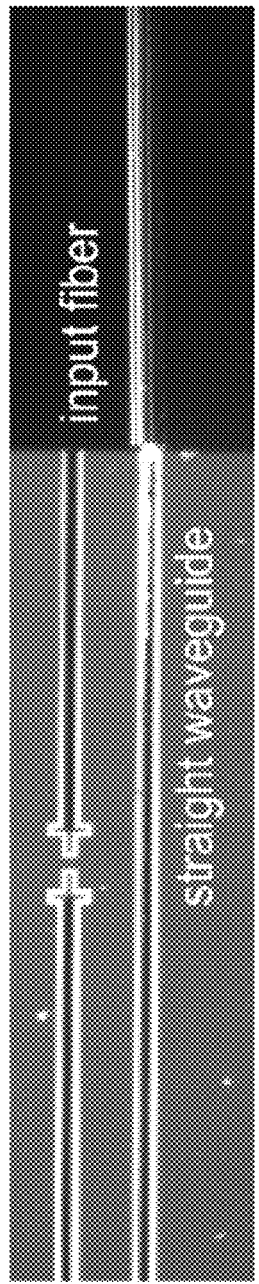
Figure 13C:
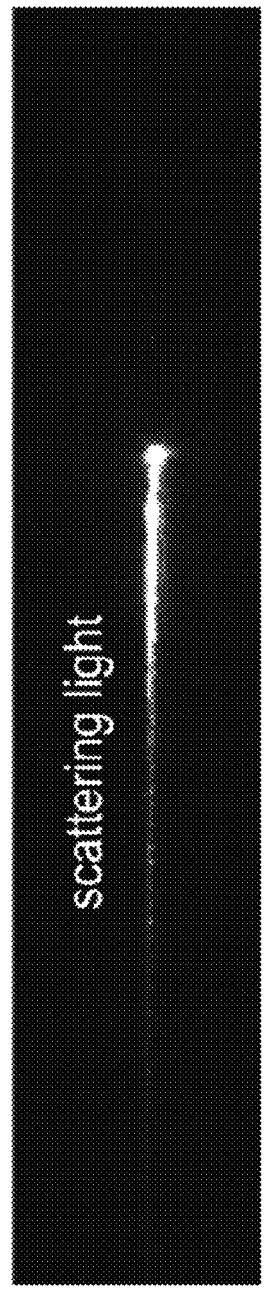

FIG. 13A shows a cross section of a device 1300 that fabricated using the method 1100 illustrated in FIGS. 11A-11D. The device 1300 includes a substrate 1310 (e.g., a silicon oxide substrate) defining an access channel 1315 (e.g., fabricated via RIE). An optical waveguide 1360 is formed within the substrate 1310 with one end of the waveguide 1360 connected to the access channel 1315. Aluminum oxide is used as the waveguide material because its refractive index is greater than the refractive index of the silicon oxide in the substrate 1310. FIG. 13B shows an SEM image of an optical waveguide butt-coupled to an optical fiber. Light at 630 nm from a laser is coupled into the optical waveguide via the optical fiber. FIG. 13C shows scattered light along the optical waveguide, illustrating waveguide losses. The laser light is coupled from the right side of the optical waveguide and propagates from right to left. As can be seen in FIG. 13C, the scattered light attenuates significantly along the length of the light waveguide, demonstrating that the laser light is well guided (i.e., confined with the light waveguide) after a short propagation distance. The estimated loss is around 60 dB/cm.

The method 1100 illustrated in FIGS. 11A-11D can be used in combination with the methods to fabricate nanofluidic channels (e.g., methods 400 in FIGS. 4A-4E, 700 in FIGS. 7A-7B, and 800 in FIG. 8) to fabricate a system including both optical waveguides and nanofluidic channels. Since both types of methods are compatible with CMOS processes, they can be used to make a complete genome mapping system on a single CMOS platform.

CMOS Genome Mapping Systems

Figure 14:
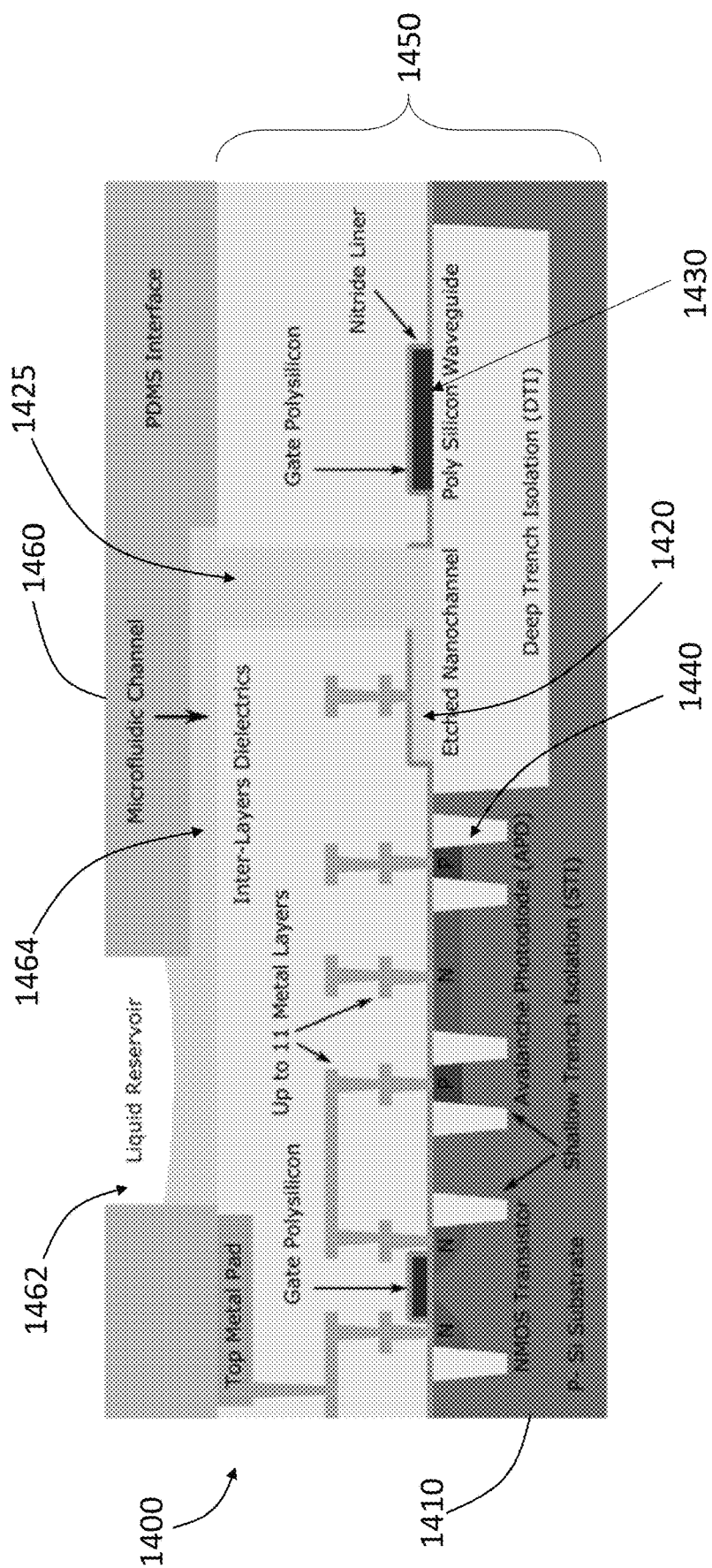
FIG. 14 shows a schematic of a molecular mapping system including a nanofluidic channel, an optical waveguide to couple excitation light beams, and a microfluidic chip to provide a sample of molecules.

FIG. 14 shows a CMOS genome mapping system 1400 including a nanofluidic chip 1450 aligned with a microfluidic chip 1460 (e.g., a PDMS microfluidic chip). The microfluidic chip 1460 includes a reservoir 1462 to store a sample of molecules and a microfluidic channel 1464 to flow the sample. The microfluidic channel 1464 is coupled to a vertical access channel 1425 in the nanofluidic chip 1450 for loading the sample into the nanofludic chip 1450.

In the nanofluidic chip 1450, a nanofludic channel 1420 is formed from a sacrificial layer in a substrate 1410 (e.g., a silicon substrate) using, for example, the method illustrated in FIGS. 4A-4E. The nanofludic channel 1420 is in fluidic communication with the vertical access 1425 to flow the sample for genome mapping. An optical waveguide 1430 is formed in close proximity to the nanofluidic channel 1420 to guide excitation light beams into the nanofludic channel 1420 so as to excite a fluorescence emission from the sample within the nanofluidic channel 1420. An APD 1440 is formed within the optical near field of the nanofluidic channel 1420 to detect the fluorescence emission.

Figures 15A, 15B, 15C, 15D, 15E, 15F:
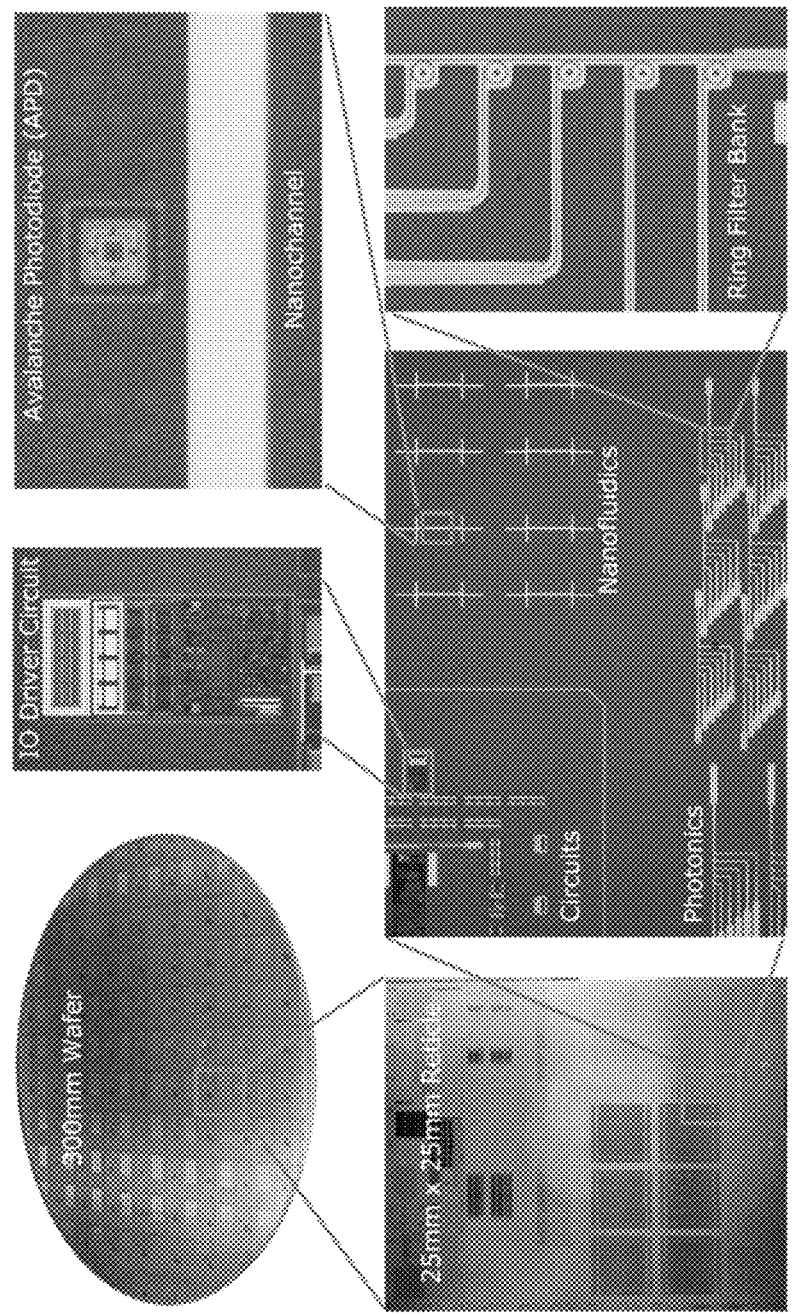
FIGS. 15A-15F are photographs of chips including integrated electronics, nanofluidic channels and reservoirs, and nanophotonic components.

FIGS. 15A-15F are photos of chips including integrated electronics, nanofluidics, and nanophtonics. FIG. 15A is a photo of an entire wafer (here, a 300 mm wafer). FIG. 15B shows one unit of the wafer shown in FIG. 15A, and FIG. 15C shows a magnified view of one section of the unit in FIG. 15B. The section in FIG. 15C includes three parts: an IO driver circuit shown in FIG. 15D, an APD fabricated near a nanofludic channel shown in FIG. 15E, and an array of ring filter banks shown in FIG. 15F. The IO driver circuit can be used to power the photodetectors (e.g. power supply) as well as to read out the detected signal. Compared to off-chip solution, integrated readout circuit can be much less prone to electromagnetic interference. Therefore, the resulting system can detect much smaller photocurrent. The array of filter banks can be used to separate light beams at different wavelengths into different channels when, for example, multi-wavelength excitation is employed to excite the fluorescence emission.

Figure 16A:
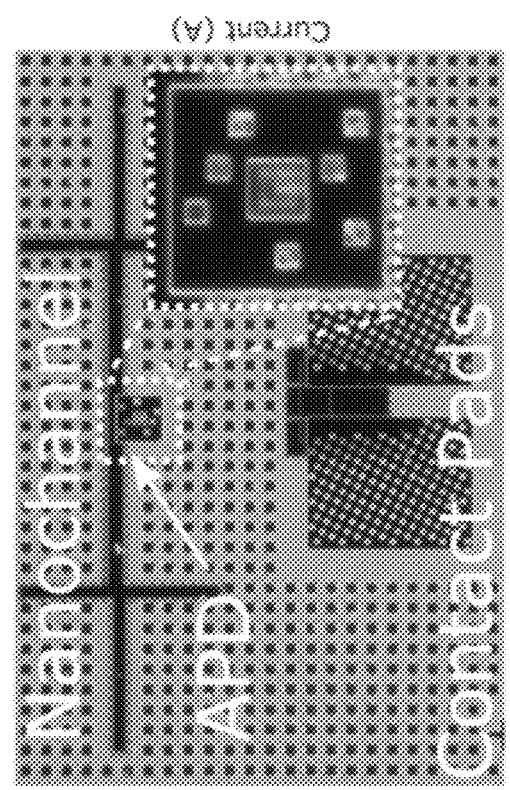
FIGS. 16A and 16B show characterization of an avalanche photodiode (APD) fabricated in close proximity to a nanofluidic channel.
Figure 16B:
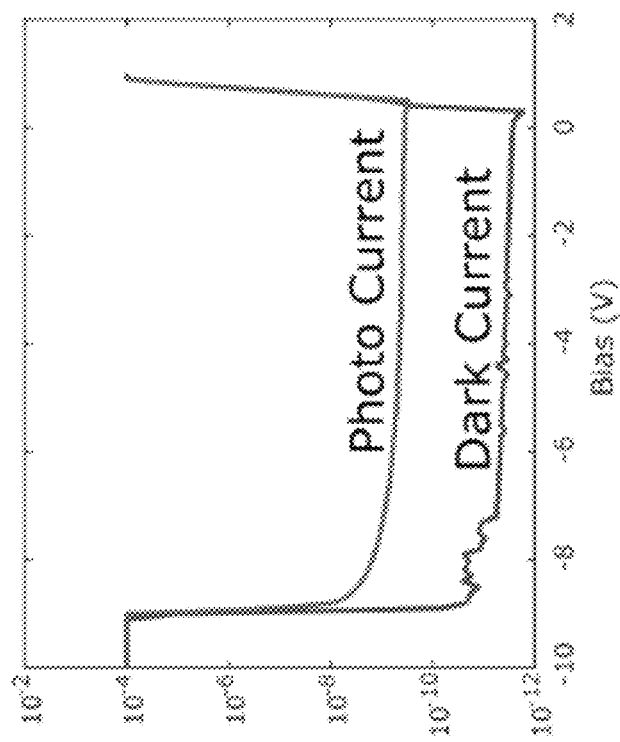

FIGS. 16A and 16B show characterization of an avalanche photodiode (APD) fabricated in the close proximity of a nanofluidic channel. FIG. 16A is a photograph of an APD and the nanofluidic channel disposed on a contact pad. FIG. 16B shows measured photocurrent and dark current of the APD. An SNR greater than 100 is observed in the test.

Figures 17A, 17B:
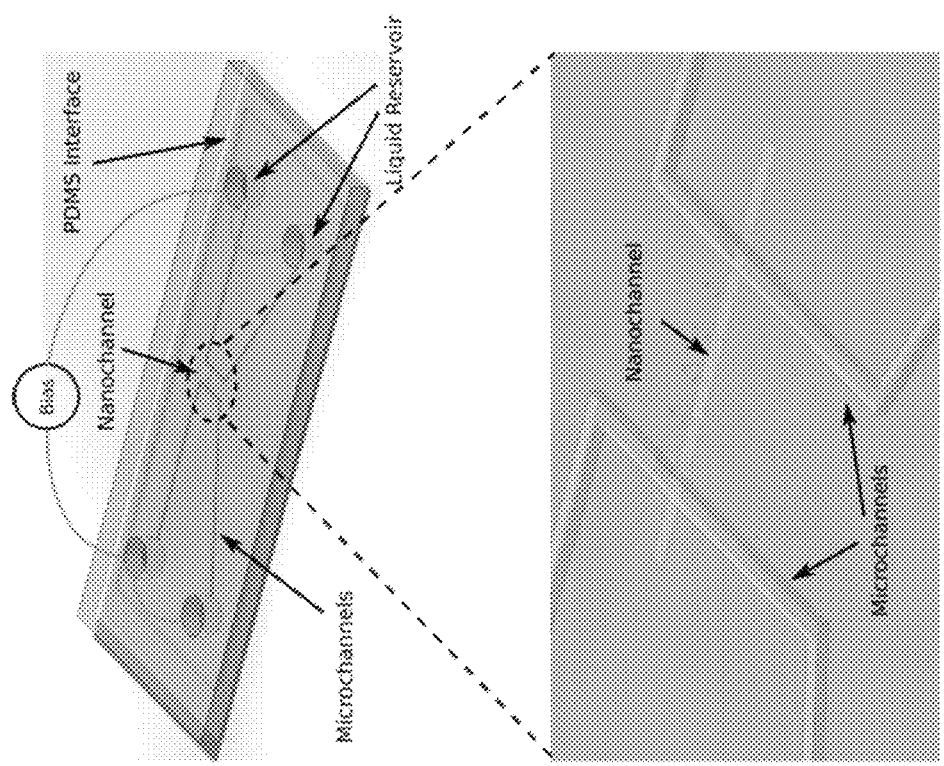
FIGS. 17A and 17B show schematics of a nanofluidic chip coupled with a microfluidic chip.

FIGS. 17A and 17B show schematics of a nanofluidic chip coupled with a microfluidic chip. The integration of nanofluidics in CMOS allows on-chip optical readout. The coupling of PDMS microfluidic interface allows connection with macroscopic devices. For example, a fluidic tubing system can be used to continuously feed and remove liquid.

Figure 18A:
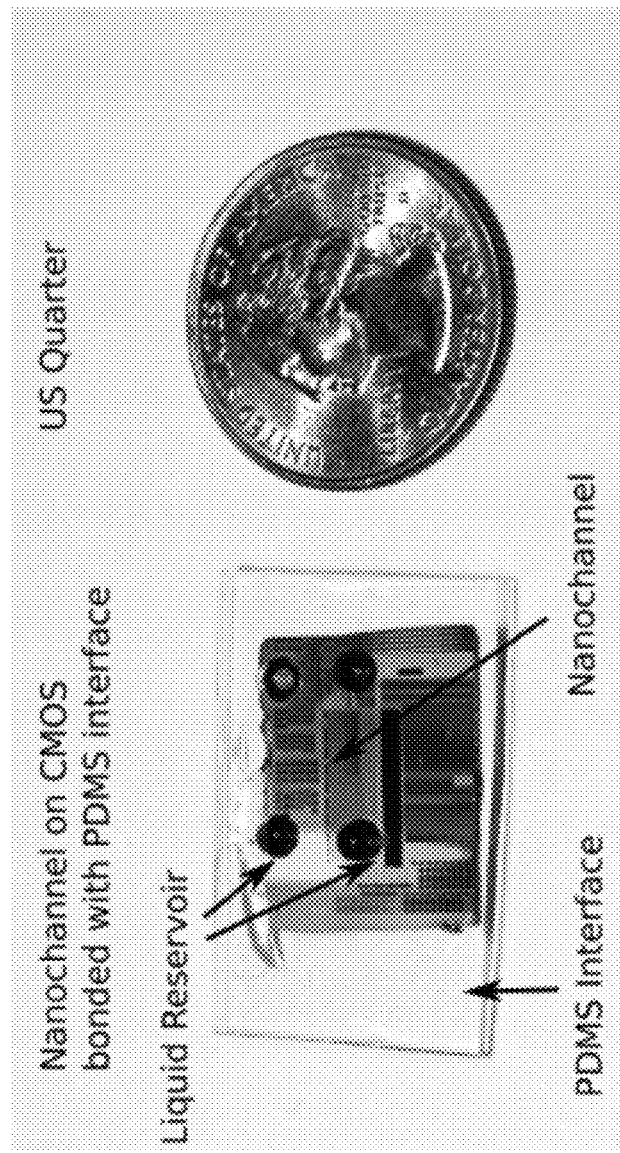
FIGS. 18A and 18B show photographs of fabricated chips for genome mapping.
Figure 18B:
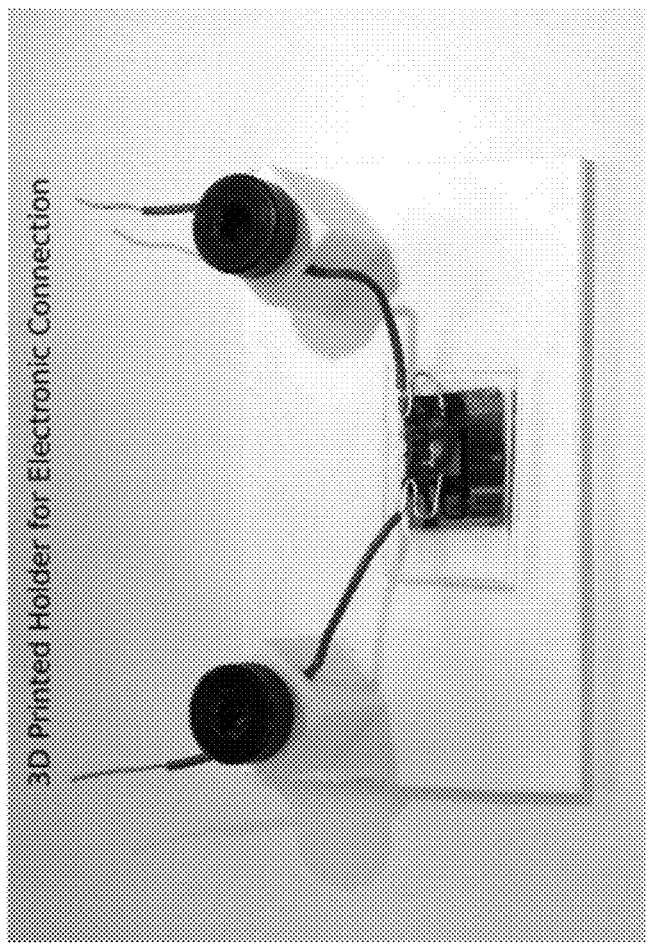

FIGS. 18A and 18B show photographs of fabricated chips for genome mapping. In FIG. 18A, a U.S. quarter is placed next to the chip to illustrate the chip's dimensions. FIG. 18B shows the chip disposed on a holder fabricated using three-dimensional (3D) printing. The holder includes connectors to electrically connect the chip with external power sources.

Figure 19:
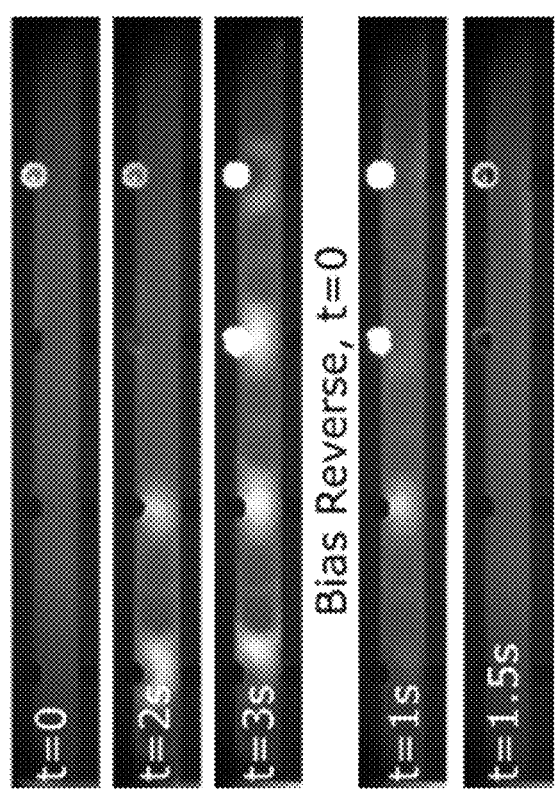
FIG. 19 shows electrical actuation of a fluorescence dye solution in a nanochannel.

FIG. 19 shows electrical actuation of fluorescence dye solution in a nanofluidic channel. In this figure, fluorescein solution is driven inside the nanofluidic channel with electrical bias. With the technique, the dye solution can be driven across the channel and back. The channel dimension is roughly 1 mm×35 μm×100 nm.

Methods of Genome Mapping

Figure 20:
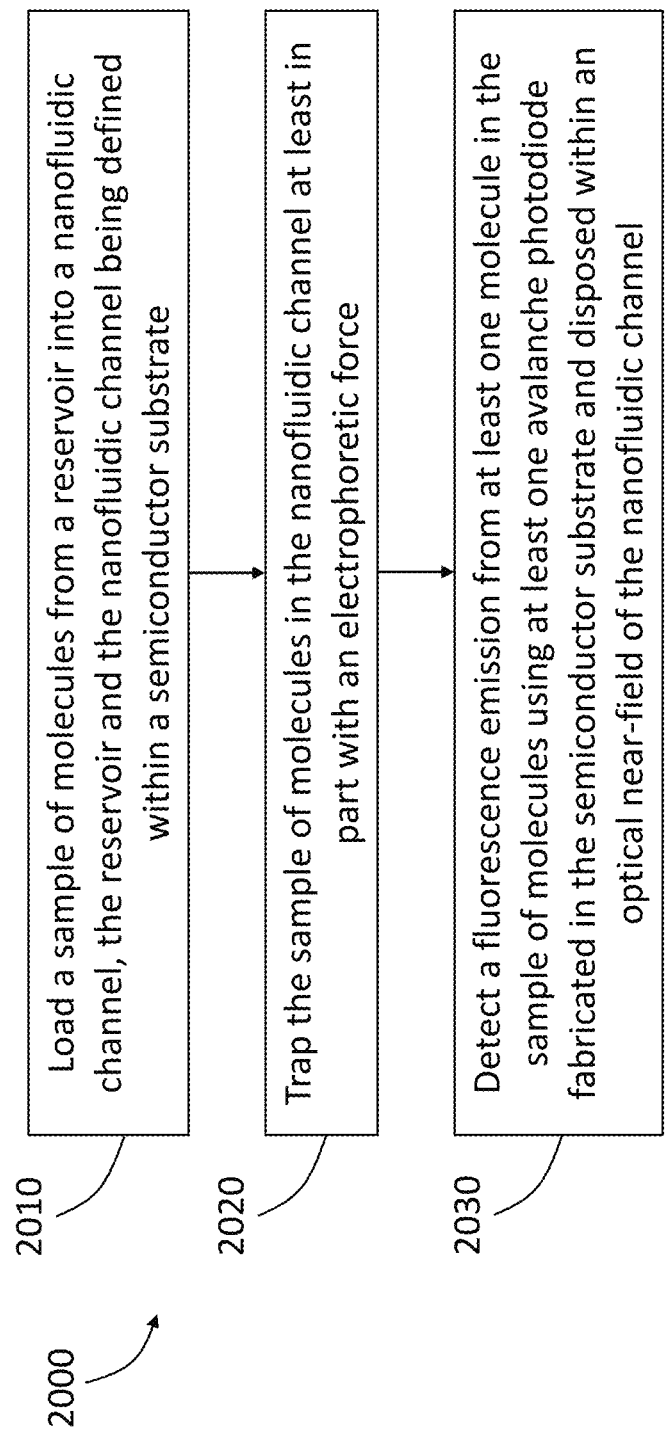
FIG. 20 illustrates a method of genome mapping using an APD disposed within an optical near field of a nanofludic channel.

FIG. 20 illustrates a method 2000 of molecular mapping (e.g., genome mapping) using an APD disposed within an optical near field of a nanofludic channel. The method 2000 includes, at 2010, loading a sample of molecules from a reservoir into the nanofluidic channel. The reservoir and the nanofluidic channel are defined within a semiconductor substrate. The method 2000 also includes, at 2020, trapping the sample of molecules in the nanofluidic channel at least in part with an electrophoretic force. The electrophoretic force can be created via electrodes disposed on the nanofluidic channel. At 2030, the fluorescence emission from at least one molecule in the sample of molecules is detected using at least one APD fabricated in the semiconductor substrate and disposed within the optical near-field of the nanofluidic channel.

The sample of molecules can include protein and/or deoxyribonucleic acid (DNA). The loading can also be facilitated via electrophoretic force. Two electrodes can be disposed on two ends of the nanofluidic channel to induce the electrophoretic force. In some examples, an alternate current (AC) voltage can be applied on the nanofluidic channel so as to trap the sample of molecules via dielectrophoretic force.

In some examples, the fluorescence emission can be coupled to the APD along a direction substantially parallel to a plane of a p-n junction in the APD. For example, the APD can include a first doped region disposed on a second doped region, and the p-n junction is at the interface of these two doped regions and substantially along the plane of the substrate. Photons in the fluorescence emission can be coupled into the APD via the side surface of the APD.

In some examples, a single APD detects the fluorescence emission. In other examples, an array of APDs disposed along the length of the nanofluidic channel detects the emission to increase the SNR of the detection. In some examples, the APD(s) can operate at a resolution finer than the diffraction limit of the fluorescence emission. This can be realized via a combination of near field imaging and particle trapping via electrophoretic force.

The method 2000 can further include exciting the fluorescence emission using excitation light beams, which can be coupled into the nanofluidic channel using one or more optical waveguides. The optical waveguides can be fabricated in the same substrate as the nanofluidic channel and APD(s) to form an integrated chip. The method to fabricate the light waveguides can be substantially similar to the method 1100 illustrated in FIGS. 11A-11D.

Conclusion

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A system for molecular mapping, the system comprising:
   a semiconductor substrate defining a reservoir to receive a sample of molecules and a nanofluidic channel in fluid communication with the reservoir;
   a plurality of electrodes, disposed on the semiconductor substrate in electrical communication with the nanofluidic channel, to electrophoretically trap the sample of molecules in the nanofluidic channel; and
   at least one avalanche photodiode, fabricated in the semiconductor substrate and disposed within an optical near-field of the nanofluidic channel, to detect fluorescence emission from at least one molecule in the sample of molecules.

2. The system of claim 1, wherein the nanofluidic channel has a width substantially equal to or less than 100 nm.

3. The system of claim 1, wherein the nanofluidic channel has a length substantially equal to or greater than 100 µm.

4. The system of claim 1, wherein the plurality of electrodes is configured to apply an alternate current (AC) voltage to the nanofluidic channel so as to trap the sample of molecules via a dielectrophoretic force.

5. The system of claim 1, wherein the at least one avalanche photodiode comprises a p-doped region having a front surface toward the nanofluidic channel and a curved back surface opposite the front surface, and the system further comprises:
   an n-doped region disposed around the back surface of the p-doped region.

6. The system of claim 5, further comprising:
   an oxide disposed between the p-doped region and the n-doped region.

7. The system of claim 1, wherein the at least one avalanche photodiode is disposed within about 50 nm to about 200 nm from the nanofluidic channel.

8. The system of claim 1, wherein the at least one avalanche photodiode comprises a p-n junction defining a plane and is configured to receive the fluorescence emission along a direction substantially parallel to the plane of the p-n junction.

9. The system of claim 1, wherein the at least one avalanche photodiode comprises a plurality of avalanche photodiodes disposed along the nanofluidic channel.

10. The system of claim 1, wherein the at least one avalanche photodiode is configured to detect the fluorescence emission with a resolution below a diffraction limit of the fluorescence emission.

11. A method of molecular mapping, the method comprising:
    loading a sample of molecules from a reservoir into a nanofluidic channel, the reservoir and the nanofluidic channel being defined within a semiconductor substrate;
    trapping the sample of molecules in the nanofluidic channel at least in part with an electrophoretic force generated by a plurality of electrodes in electrical communication with the nanofluidic channel; and
    detecting a fluorescence emission from at least one molecule in the sample of molecules using at least one avalanche photodiode fabricated in the semiconductor substrate and disposed within a distance from the nanofluidic channel that is less than a wavelength of the fluorescence emission.

12. The method of claim 11, wherein loading the sample of molecules comprises loading a protein into the nanofluidic channel.

13. The method of claim 11, wherein loading the sample of molecules comprises loading deoxyribonucleic acid (DNA) into the nanofluidic channel.

14. The method of claim 11, wherein trapping the sample comprises applying an alternate current (AC) voltage on the nanofluidic channel so as to trap the sample of molecules via dielectrophoretic force.

15. The method of claim 11, wherein detecting the fluorescence emission comprises receiving the fluorescence emission along a direction substantially parallel to an interface between a p-doped region and an n-doped region of a p-n junction in the at least one avalanche photodiode.

16. The method of claim 11, wherein detecting the fluorescence emission comprises detecting the fluorescence emission using an array of avalanche photodiodes disposed along the nanofluidic channel.

17. The method of claim 11, wherein detecting the fluorescence emission comprises detecting the fluorescence emission with a resolution below a diffraction limit of the fluorescence emission.

18. The method of claim 11, further comprising:
    exciting in the at least one molecule to elicit the fluorescence emission.

19. The method of claim 18, wherein the exciting further includes exciting the molecule using a laser pulse from a laser source, the method further comprising synchronizing a bias of the avalanche photodiode with timing of the laser pulse to reduce or prevent detection of the laser pulse, by the avalanche photodiode, due to scattering of the laser pulse.

20. The method of claim 19, wherein the synchronizing includes:
    recording timing information for the laser pulse;
    estimating a time range for the detecting the fluorescence emission; and
    biasing the avalanche photodiode to prevent its operation outside the time range.

21. A system for molecular mapping, the system comprising:
    a semiconductor substrate defining a reservoir to receive a sample of molecules and a nanofluidic channel having a width substantially equal to or less than 100 nm and in fluid communication with the reservoir;
    a plurality of electrodes, disposed on the semiconductor substrate in electrical communication with the nanofluidic channel, to electrophoretically trap the sample of molecules in the nanofluidic channel; and
    at least one avalanche photodiode, fabricated in the semiconductor substrate and disposed within 800 nm of the nanofluidic channel, to detect fluorescence emission from at least one molecule in the sample of molecules, wherein:
    the at least one avalanche photodiode comprises a p-doped region and an n-doped region and configured to receive the fluorescence emission along a direction substantially parallel to an interface between the p-doped region and the n-doped region, and
    the at least one avalanche photodiode is configured to detect the fluorescence emission with a resolution below a diffraction limit of the fluorescence emission.

* * * * *